United States Patent [19]
Sugiyama et al.

[11] Patent Number: 5,579,112
[45] Date of Patent: Nov. 26, 1996

[54] OPTICAL TOMOGRAPHIC IMAGING EQUIPMENT HAVING A LIGHT SOURCE UNIT FOR GENERATING A LIGHT WAVE HAVING A PREDETERMINED COHERENCE LENGTH

[75] Inventors: Yuiti Sugiyama; Junji Miyazaki, both of Yamagata, Japan

[73] Assignee: Biophotonics Information Laboratories Ltd., Yamagata, Japan

[21] Appl. No.: 329,978

[22] Filed: Oct. 27, 1994

[30]     Foreign Application Priority Data

Mar. 28, 1994  [JP]  Japan .................................. 6-057137

[51] Int. Cl.[6] ..................................................... G01B 9/02
[52] U.S. Cl. ........................................... 356/360; 356/345
[58] Field of Search ..................................... 356/360, 349, 356/345

[56]          References Cited

U.S. PATENT DOCUMENTS 4,140,022  2/1979  Maslak ........................................ 73/626

FOREIGN PATENT DOCUMENTS

WO92/19930  11/1992  WIPO.

*Primary Examiner*—Frank Gonzalez
*Assistant Examiner*—Amanda Merlino
*Attorney, Agent, or Firm*—Staas & Halsey

[57]           ABSTRACT

An optical tomographic imaging equipment including a light-receiving unit having a plurality of light-receiving elements, and an electronic focusing control unit. The electronic focusing control unit provides a control such that a plurality of light-receiving signals, derived by light-receiving an interference wave involved in superposition of the reflected light and the reference light using the plurality of light-receiving elements of the light-receiving unit, are relatively delayed and added to each other so as to issue resultant light-receiving signals involved in emphasis of information of a predetermined point on a light path of the object light within the subject.

26 Claims, 19 Drawing Sheets

OPTICAL TOMOGRAPHIC IMAGING EQUIPMENT HAVING A LIGHT SOURCE UNIT FOR GENERATING A LIGHT WAVE HAVING A PREDETERMINED COHERENCE LENGTH

BACKGROUND OF THE INVENTION

1. Field of the Invention

The present invention relates to an optical tomographic imaging equipment adapted to image tomographic images of the subject, specifically a biological sample on a non-invasive basis, and more particularly, to an optical tomographic imaging equipment in which a beam of light is projected to the subject and the light scattered and reflected within the subject is received so that a light-receiving signal, which carries a tomographic image of the subject, can be derived.

2. Description of the Related Art

Hitherto, for observing a tomographic image of the subject, specifically a biological sample, various types of equipment have been known which are based on various principles.

For example, there has been known an ultrasonograph in which an ultrasonic wave is applied to the subject and the ultrasonic echoes reflected by tissues in the subject are received so as to derive an ultrasound-receiving signal. In such an ultrasonograph, a tomographic image of the subject is displayed on the basis of the thus derived ultrasound-receiving signal. This type of ultrasonograph is put to practical use for diagnoses of diseases of, for example, the heart and the abdomen. However, the resolution of the tomographic image is of the order of several hundreds of $\mu$ meters in terms of the actual size of the subject. The order of several hundreds of $\mu$ meters is short not less than one figure (digit) in a degree of a lack of resolution to observe in detail a tissue system of a biological sample.

Further, as a device for irradiating beams of light into the subject, there is known a confocal laser scanning ophthalmoscope (hereinafter referred to as "CLSO"). The CLSO adopts a scheme in which a laser beam sequentially scans on a predetermined depth within the subject on a two dimensional basis, or on a three dimensional basis including a direction of the depth, and rays of light reflected from the respective focal points are separately extracted through a pinhole from rays of light reflected from the locations of the depth other than the focal points, so that the extracted rays of light are received. According to this CLSO, it is possible to obtain a two dimensional tomographic image in a short time, such as several tens of m seconds, which image is provided with the resolution as to the horizontal direction (Y direction) of the order of $10\mu$ meters. However, the resolution as to the vertical or depth direction (Z direction) is simply of the order of several hundreds of $\mu$ meters. This order is short not less than one figure (digit) in a degree of a lack of resolution to observe in detail a tissue system of a biological sample.

In view of the foregoing, there has been proposed equipment (refer to PCT/ US92/03536) which is capable of deriving a tomographic image with the resolution of the order of several $\mu$ meters with respect to both the Z direction (depth direction) and the Y direction (horizontal direction).

FIG. 26 is a view useful for understanding the above referenced equipment.

Light emanating from a light source emitting light with a short coherence length, for example, a SLD (Super Luminescent Diode) 111, is transmitted through an optical fiber 112 and divided by a fiber coupler 113 into a first light wave (object light) and a second light wave which are transmitted through optical fibers 114 and 115 via an objective lens system 117 and a reference lens system 118 to the subject 119 and a reference mirror 120, respectively. The reference mirror 120 is moving in the Z direction (direction of an optical axis of the light beam), while the system is operative.

According to the system shown in FIG. 26, there is provided a PZT (Piezo-electric Transducer) at the object light side to conduct a frequency shift of the object light. The PZT is used so as to obtain at a photo-diode 122, which will be described later, a signal having a frequency suitable for the photo-diode 122 or a signal processing system including the photo-diode 122. However, the PZT is not always needed in view of a principle of the measurement of the system. Thus, an explanation of the operation of the PZT 116 will be omitted and a system having no PZT 116 will be described hereinafter.

The beam of light irradiated onto the subject 119 travels inside of the subject 119, and will be reflected by various points on a traveling path of the beams within the subject. The reflected light is introduced via the objective lens system 117 to the optical fiber 114, and further transmitted via the fiber coupler 113 through an optical fiber 121 to a photo-detector, for example, the photo-diode 122.

Likely, the light reflected from the reference mirror 120 is introduced via the reference optical system 118 to the optical fiber 115, and further transmitted via the fiber coupler 113 through an optical fiber 121 to the photo-diode 122.

FIG. 27 is a view illustrating a signal derived from the photo-diode 122.

The axis of abscissa of the figure corresponds to the location in the Z direction of the reference mirror 120, and also represents a time basis since the reference mirror 120 is moving at constant speed in the Z direction, while the system is operative. The axis of the ordinates of the figure represents an amplitude of a light-receiving signal of the photo-diode 122. A dashed line is representative of the envelope of the light-receiving signal. The signal shown in FIG. 27 will be obtained on the assumption that the reflection of light occurs by only a point within the subject and, in addition, the reflected light and the reference light, which are transmitted to the photo-diode 122, are even in intensity of light.

When the reference mirror 120 is moved continuously at a constant speed in the Z direction, the reference light reflected by the reference mirror 120 is modulated to light of which a frequency transitions by the corresponding Doppler frequency in comparison with the incident light to the reference mirror 120. Consequently, there will occur an interference between the reflected light and the reference light on the photo-diode 122, and thus there will be observed a signal having a frequency given with a difference between the frequency of the reflected light and the frequency of the reference light.

By the way, assuming that the light emitted from the SLD 111 is short in the coherence length and the reflection occurs at only a certain single point of the subject 119, there is observed a burst wave, as shown in FIG. 27, which appears with the origin 0 in the center over only the width in the Z direction (or time interval) corresponding to the coherence length of light emitted from the SLD 111, where an optical path (optical distance), wherein light emitted from the SLD 111 is projected in the form of the object light onto the subject and reflected by a certain point of the subject, and reaches the photo-diode 122, is completely the same as an optical path, wherein light emitted from the SLD 111 is reflected by the reference mirror 120, and reaches in the form of the reference light the photo-diode 122. Actually, reflections occur on various points along the light path of the beam of light travelling inside of the subject 119. Therefore, when the reference mirror 120 is moved in the Z direction, it is possible to derive signals wherein information messages as to the reflection light inside of the subject 119 are sequentially extracted in compliance with the position of the reference mirror 120 in the Z direction at the respective time points during the movement of the reference mirror 120. The full-width-half-maximum (FWHM) of the burst wave in the Z direction in case of reflection from a single point, as shown in FIG. 27, is given with about 10 μ meters or less. Thus the resolution of 10μ meters or less is obtained with respect to the Z direction (depth direction).

On the other hand, the resolution as to the Y direction (horizontal direction) depends on a degree of reduction of the object beam of light on the reflecting points within the subject 119. In order to obtain the resolution of the order of 10μ meters also with regard to the Y direction (horizontal direction), it is necessary to reduce a diameter of the beam at the respective reflecting points to the order of 10μ meters. Hence, the objective lens system 117 is equipped with a focusing system. The focusing system is moved in synchronization with the movement of the reference mirror 120 in the the Z direction in such a manner that the object light is converged at the reflecting point within the subject 119 corresponding to the associated location of the reference mirror 120 in the Z direction, so that the focal point of the objective lens system 117 is moved in the Z direction.

In this manner, when the reference mirror 120 is moved in the Z direction, while the focal point of the objective lens system 117 is adjusted, it is possible to derive a line of signal of a tomographic image along a piece of beam of light extending inside of the subject 119. This line is referred to as a scanning line.

The light-receiving signal derived from the photo-diode 122 is supplied to a detector circuit 123 to be subjected to detection in which a signal corresponding to the envelope shown in FIG. 27 is extracted. An A/D converter 124 converts the detected signal from the detector circuit 123 into a digital signal. An output of the A/D converter 124 is applied to a computer 125. Thus, the computer 125 receives image data representative of a tomographic image along a piece of the scanning line.

The objective lens system 117 is movable in the Y direction (scanning direction). When the above-mentioned scanning is repeatedly performed while the objective lens system 117 is moved, the computer 125 receives image data representative of a tomographic image along a two dimensional section consisting of a component as to a depth direction (Z direction) of the subject 119 and a component as to a movement direction (Y direction) of the objective lens system 117. The computer 125 practices a predetermined image processing for the received image data as the occasion demands. Thereafter, a tomographic image involved in the processed image data is displayed on a display unit (not illustrated), or a hard copy of the tomographic image is produced by a hard-copy apparatus.

While the equipment or system shown in FIG. 26 adopts the optical fibers 112, 114, 115 and 121, it should be noted that each of these elements is exemplarily shown as means for transferring light and it is not always needed to use the optical fibers, in view of a principle of formation of the tomographic image which has been explained above referring to FIG. 26.

Incidentally, the above-mentioned proposal includes a system in which a frequency of light source is modulated, instead of a mechanical scanning in the depth direction (Z direction). According to such a system, however, it takes much time for signal processing after light is received by the photo-diode 122, and further it is difficult to converge a light beam on various depth positions. Thus, the system is of a fixed focus. This causes a degradation of the resolution of areas out of the fixed focus point with respect to the lateral direction (Y direction). Consequently, it is difficult to obtain a high resolution of a tomographic image as a whole.

As apparent from the above description, according to the conventional system as explained referring to FIGS. 26 and 27, it is possible to obtain a tomographic image of the subject with the resolution of the order of 10μ meters with regard to both the depth direction (Z direction) and the horizontal direction (Y direction).

However, in general, it is difficult to maintain a fine beam within a scattering medium covering a wide field with respect to the depth direction. While the enlargement of the aperture makes it possible to provide a fine beam at the focus point, this permits the beam to rapidly spread. Thus, according to the fixed focus, it is difficult to obtain an even fine beam extending over a wide field. Further, if the aperture is enlarged, it is difficult to attain a high resolution only through simply switching a plurality of transmitter and receiver units. Thus, a mechanical positioning apparatus is needed. There is a technology such that beams are swung at a high speed with a rotary mirror, a galvano-mirror or the like. However, this technology also needs a mechanical positioning apparatus to attain a variable focus in a depth direction.

Hence, it is necessary that as shown in FIG. 26 there are provided a focusing system which is an extremely large optical system in comparison with the reference mirror 120, and in addition the objective lens system 117 having a large aperture, and these systems are moved in synchronism with the movement of the reference mirror 120. It is difficult to move those systems at high speed, and thus it takes a lot of time to derive a light-receiving signal along a scanning line. Further, with respect to the objective lens system 117, it is necessary to move this system also in a Y direction. As a result, it would take a long time to make up a piece of two-dimensional tomographic imaging data. While the taking of much time to issue the tomographic image is a problem itself, it causes the following drawbacks. For example, in a case where the subject is a biological sample in vivo, the subject will significantly move during the time required for obtaining the tomographic image. Thus, it is difficult to obtain a proper tomographic image at a certain point of time.

Further, the objective lens system 117 is constituted of, for example, a lens group equipped with a focusing system. In addition, it is necessary to provide a mechanism for moving the objective lens system 117 also in the Y-direction. Consequently, if it is intended to implement the apparatus shown in FIG. 26, the apparatus involves such a problem that the mechanism of the apparatus becomes complicated and the apparatus is of a large size. These drawbacks result in reduced reliability, and the apparatus becomes expensive.

SUMMARY OF THE INVENTION

In view of the foregoing, it is therefore an object of the present invention to provide optical tomographic imaging equipment capable of obtaining a tomographic image at high speed, and maintaining a high resolution with respect to both the depth direction and the scanning direction.

To achieve the above-mentioned objects, according to the present invention, there is provided an optical tomographic imaging equipment comprising:

(1) a light source unit, having a light source for radiating a light wave having a predetermined coherence length, for splitting the light wave radiated from said light source into a first light wave and a second light wave and emitting the same;

(2) a light-receiving unit having a plurality of light-receiving elements;

(3) an object unit for introducing the first light wave emitted from said light source unit into a subject in the form of an object light irradiating the subject, and also introducing into said light-receiving unit a reflected light obtained through reflection of the object light from the subject;

(4) a reference light generating unit for converting the second light wave received from said light source unit into a reference light whose frequency is shifted from that of the second light wave through continuously varying an optical path as a travelling path of the second light wave up to said light-receiving unit, and introducing the reference light to said light-receiving unit in such a way that at least part of the reference light is superposed on the reflected light in said light-receiving unit; and (5) an electronic focusing control unit for providing such a control that a plurality of light-receiving signals, which are derived by means of light-receiving an interference wave involved in superposition of the reflected light and the reference light with said plurality of light-receiving elements of said light-receiving unit, are relatively delayed and added to each other so as to issue light-receiving signals involved in the emphasis of information of a predetermined point on a light path of the object light within the subject.

Incidentally, it is noted that the above-referenced elements (1)–(5) denote portions as a functional concept. In an actual structure, it is acceptable that, for example, a certain single member serves as plural ones of the elements (1)–(5), and also that plural ones of the elements (1)–(5) are integrally arranged, not separately. For example, the present invention includes such an arrangement that a beam splitter serves to split the light wave into the first light wave and the second light wave as in the light source unit as the above-referenced element (1), and in addition serves as the object unit (3).

(6) In the equipment according to the present invention as described above, it is preferable that said light source unit has scanning means for sequentially varying an emission position of the first light wave so that a scan of the subject by the object light can be conducted.

(7) In the above case, it is preferable that said light source unit has a plurality of light sources adapted for supplying a plurality of said object lights mutually deviated from each other in the light path, and the scan of the subject by the object light is conducted through sequentially turning on said plurality of light sources.

(8) It is preferable that said light source unit has an optical fiber for transmitting the light wave emitted from said light source.

(9) In the above case, it is acceptable that said light source unit has a fiber-coupler for splitting the light wave transmitted via said optical fiber into the first light wave and the second light wave, said fiber-coupler being disposed in mid course of said optical fiber.

(10) In the above case, it is preferable that optical fiber portions, through which the first light wave and the second light wave are transmitted, respectively, have the same length of optical path as each other.

(11) In the equipment according to the present invention as described above, it is acceptable that said light source unit has a collimating optical system in which the second light wave is emitted in the form of a collimated beam toward said reference light generating unit (4), and said reference light generating unit has an optical fiber adapted to emit the reference light from its one end in the form of beam spreading in a cone shape, and an incident optical system in which the second light wave in the form of a collimated beam is converged and enters through the other end of said optical fiber.

(12) Further, in the equipment according the present invention as described above, it is preferable that said reference light generating unit (4) has a scattering optical system having an average surface roughness which is finer than a center wavelength of the light wave.

(13) Further, in the equipment according the present invention as described above, it is preferable that said plurality of light-receiving elements of said light-receiving unit (2) is arranged in a scanning direction in which the reflected light travels on said light-receiving unit in response to a scan of the subject by the object light.

(14) With respect to said reference light generating unit (4), it is preferable that said reference light generating unit is movable in accordance with an operation of varying an optical path of the reference light, and has a cylindrical optical system, for correcting the optical path of the reference light introduced into said light-receiving unit with respect to a thickness direction intersecting the scanning direction.

(15) Further, in the equipment according the present invention as described above, it is acceptable that said plurality of light-receiving elements of said light-receiving unit is arranged on a two-dimensional basis both in a scanning direction in which the reflected light travels on said light-receiving unit in response to a scan of the subject by the object light, and in a thickness direction intersecting the scanning direction, and said electronic focusing control unit provides such a control that the plurality of light-receiving signals are relatively delayed and added to each other with respect to both the scanning direction and the thickness direction.

(16) With respect to said electronic focusing control unit (5), it is preferable that said electronic focusing control unit provides a control such that the plurality of light-receiving signals is delayed and added to each other while sequentially varying a relative delay pattern so as to issue light-receiving signals involved in emphasis of information of a plurality of predetermined points aligned on a scanning line extending to a light path of the object light irradiated on the subject.

(17) With respect to said electronic focusing control unit (5), it is acceptable that said electronic focusing control unit provides a control such that the plurality of light-receiving signals is delayed and added to each other while sequentially varying a relative delay pattern so as to issue light-receiving signals involved in emphasis of information of a plurality of predetermined points aligned on each of a plurality of scanning lines extending to a light path of the object light.

(18) With respect to said electronic focusing control unit (5), it is acceptable that said electronic focusing control unit provides a control such that with respect to each of a plurality of said object lights according to the light waves emitted from said plurality of light sources, the plurality of light-receiving signals is delayed and added to each other while sequentially varying a relative delay pattern so as to issue light-receiving signals involved in emphasis of information of a plurality of predetermined points aligned on each of a plurality of scanning lines extending to a light path of the object light.

(19) Further, in the equipment according the present invention as described above, it is acceptable that said light source unit simultaneously emits a plurality of said object lights each of which is mutually different from each other in their light paths, and said electronic focusing control unit provides such a control that the plurality of light-receiving signals is delayed and added to each other while sequentially varying a relative delay pattern so as to issue light-receiving signals involved in emphasis of information of a plurality of predetermined points aligned on each of a plurality of scanning lines extending to the plurality of the light paths of object lights, and at least one scanning line extending to each light path of each object light.

(20) Further, in the equipment according to the present invention as described above, it is acceptable that said electronic focusing control unit has a plurality of delay lines each adapted to delay on a variable delay amount basis the associated one of the light-receiving signals derived from said plurality of light-receiving elements.

(21) Further, in the equipment according to the present invention as described above, it is acceptable that said electronic focusing control unit has delay means for delaying said light-receiving signals on a variable delay amount basis by a weighting addition on a variable weighted amount basis, wherein said electronic focusing control unit divides each of the light-receiving signals derived from said plurality of light-receiving elements into a pair of divided signals to produce an associated one signal and an associated other signal, and delays one of the pair of divided signals by a predetermined delay amount with respect to that of the other of the pair of divided signals, and operates an associated weighting operation on a variable weighted amount basis to produce the associated one signal, and operates an associated weighting operation on a variable weighted amount basis to produce the associated other signal, and adds those signals to produce an associated addition signal.

(22) Further, in the equipment according the present invention as described above, it is acceptable that said electronic focusing control unit has pairs of weighted adder means as a part of delay and addition means, wherein first ones of the pairs of the weighted adder means perform a weighting addition on a variable weighted amount basis for each of the light-receiving signals derived from said plurality of light-receiving elements, to produce associated one addition signals and second ones of the pairs of weighted adder means perform a weighting addition on a variable weighted amount basis for each of the light-receiving signals to produce associated other addition signals, and delay and addition means for delaying the associated one addition signals by a predetermined delay amount with respect to that of the associated other addition signals and adding those signals.

(23) Further, in the equipment according to the present invention as described above, it is preferable that said light-receiving unit or said electronic focusing control unit has an aperture definition means for optionally defining a light-receiving aperture comprising said light-receiving elements for obtaining the light-receiving signals to be added to each other by said electronic focusing control unit, said aperture definition means comprising at least part of plural light-receiving elements among the plurality of light-receiving elements provided on said light-receiving unit.

(24) In the above case, it is acceptable that said plurality of light-receiving elements of said light-receiving unit are arranged in a scanning direction in which the reflected light travels on said light-receiving unit in response to a scan of the subject by the object light, and said light-receiving unit is provided with a CCD having read circuits for outputting the light-receiving signals derived from the light-receiving elements within the light-receiving aperture which are movably set up, said light-receiving aperture comprising at least part of plural light-receiving elements selected from among the plurality of light-receiving elements provided on said light-receiving unit.

(25) It is acceptable that said electronic focusing control unit has a plurality of variable gain amplifiers for defining said light-receiving aperture and each variably amplifying the light-receiving signal derived from the associated one of the plural light-receiving elements within said light-receiving aperture.

(26) It is acceptable that said electronic focusing control unit has a plurality of A/D converters each for converting the light-receiving signal in the form of an analog signal derived from the associated one of said plurality of light-receiving elements into a digital light-receiving signal, and delay and addition operation means for relatively delaying and adding the digital light-receiving signals derived from said plurality of A/D converters.

(27) In the above case, it is preferable that said electronic focusing control unit has an aperture definition means for optionally defining a light-receiving aperture for obtaining the light-receiving signals to be added to each other by said delay and addition operation means on the basis of said digital light-receiving signals, said light-receiving aperture comprising at least part of plural light-receiving elements among the plurality of light-receiving elements provided on said light-receiving unit.

(28) It is preferable that said delay and addition operation means relatively delays said digital light-receiving signals, which are derived from the plurality of light-receiving elements constituting the light-receiving aperture defined by said aperture definition means and are subjected to the digital conversion by said A/D converters, and in addition, performs a weighting addition on a variable weighted amount basis.

(29) It is preferable that said object unit (3) is equipped with a correction plate according to the subject for correcting the light paths of said object light and/or said reflected light, said correction plate being fixed or interchangeably mounted on said object unit.

(30) Further, in the equipment according the present invention as described above, it is acceptable that the equipment further comprises a display unit adapted to display tomographic images of the subject on the basis of the light-receiving signals involved in emphasis of information of the plurality of predetermined points.

The optical tomographic imaging equipment according to the present invention is basically different from the prior art (FIG. 26) in the point that the equipment is provided with the electronic focusing control unit (5). More specifically, according to the present invention, the light-receiving unit (2) has a plurality of light-receiving elements, and the electronic focusing control unit provides such a control that a plurality of light-receiving signals, which are derived by means of light-receiving interference waves involved in superposition of the reflected light and the reference light with the plurality of light-receiving elements of the light-receiving unit, are relatively delayed and added to each other (this may be referred to as "delay and addition") so as to issue light-receiving signals involved in emphasis of information of a predetermined point on an optical path of the object light within the subject. Even if a light beam is not converged at the predetermined point, it is possible through the delay and addition to derive signals equivalent to the event that a small light beam spot (for example, a light spot with a diameter of the order of 10 μm) is formed at the predetermined point. This theory will be explained referring to the drawing in conjunction with the preferred embodiments of the present invention later.

The present invention will now be explained in comparison with the prior art shown in FIG. 26. According to the present invention, there is no need to provide a focus point moving system for moving a focus point of the objective lens system 117 in the Z-direction, and it is not necessary to provide such a large type of lens system. It is sufficient for a scan in the Y-direction (lateral direction) to dispose an optical fiber (the above-mentioned item (8)) having, for example, a several ten μm of edge and travel an emission end of the optical fiber in the Y-direction (the above-mentioned item (6)). Alternatively, it is acceptable to arrange a plurality of optical fibers in the Y-direction and sequentially switch over those fibers (the above-mentioned item (7)). With respect to the Z-direction, it is sufficient for the mechanical movement to travel the reference mirror 120 which is not heavy. If there is practiced such an electric processing that a delay pattern in the delay and addition processing is sequentially varied in accordance with the movement of the mirror 120, it is possible to derive signals which are involved in emphasis of information at a plurality of predetermined points along the scanning line, and also to obtain the tomographic image at high speed in its entirety even in a sheet of a two-dimensional tomographic image.

While light beams are not indeed converged at the predetermined point, there is produced the signal which corresponds in equivalence to that, the light beams are converged at the predetermined point through selection of the interference with the reference light and the delay and addition processing. Thus, it happens that such a predetermined point is referred to as a "focus point".

With respect to the delay and addition to form such a focus point, in principle, it is preferable to provide such an arrangement that a plurality of light-receiving elements or photo-electric elements are arranged on a two-dimensional basis in both the Y-direction (lateral direction or scanning direction) and the thickness direction (it happens that this is referred to as the "X-direction") of the two-dimensional tomographic image which intersects the Y-direction, and to perform the delay and addition with respect to both the directions, that is, the Y-direction and the X-direction (refer to the above-mentioned item (15)). However, the two-dimensional delay and addition processing is complicated in processing and needs a larger scale of circuit. In view of this drawback, it is acceptable to provide an arrangement such that a plurality of light-receiving elements is arranged on a one-dimensional basis in the Y-direction (lateral direction), and to perform the delay and addition with respect to only the Y-direction (refer to the above-mentioned item (13)). In case of the delay and addition processing as to only the Y-direction (scanning direction), it is possible to enhance the resolution with respect to the X-direction (thickness direction) by means of a cylindrical lens having a focus in respect of the X-direction (thickness direction).

In this manner, according to the optical tomographic imaging equipment of the present invention, it is possible to form the scanning lines through an electric processing. Therefore, it is possible to form a plurality of scanning lines in a piece of an object light beam, since the object light has generally a finite beam width (refer to the above-mentioned items (17) and (18)). Further, for high speed scanning, it is acceptable to provide such an arrangement that a plurality of object light beams is simultaneously formed, and the light-receiving signals are delayed and added in such a manner that a single or plural scanning lines are formed in each of the plurality of the object light beams (refer to the above-mentioned items (18) and (19)).

According to the optical tomographic imaging equipment of the present invention, to implement the delay and addition processing, it is acceptable to adopt any delay means. For example, the delay line (the above-mentioned item (20)) may be adopted to delay the light-receiving signals. Further, it is acceptable to conduct the delay (the above-mentioned item (21)) or the delay and addition (the above-mentioned item (22)). Still further, it is acceptable to conduct the delay and addition according to the digital signal processing (the above-mentioned item (26)).

According to the diffraction theory, in order to obtain the same resolution in both the cases of focusing on the shallow position of the subject (as mentioned above, actually, the delay and addition are conducted with a delay pattern suitable for the shallow position) and of focusing on the deep position of the subject, it is necessary to vary the light-receiving aperture (an aperture comprising a plurality of light-receiving elements or photo-electric elements for effectively receiving the interference light). It is preferable to move the light-receiving aperture in the Y-direction in synchronism with the scan in the Y-direction by the object light.

Consequently, in the optical tomographic imaging equipment according to the present invention, it is preferable to provide aperture definition means for optionally defining the light-receiving aperture (refer to the above-mentioned items (23) and (27)).

The light-receiving signals derived from the plurality of light-receiving elements constituting the light-receiving aperture are added each other in the delay and addition operation with weight in such a manner that a relatively small weight is applied to the light-receiving signals derived from the light-receiving elements located at the edges of the light-receiving aperture, while a larger weight is applied to the light-receiving signals derived from the light-receiving elements located at the center of the light-receiving aperture, in accordance with a so-called apodization (refer to the above-mentioned items (25) and (28)). Thus, it is possible to reduce the secondary beams (a so-called side lobe) which will be formed around the main beam extending along the scanning line.

Further, according to the present invention, it is preferable to provide a correcting plate according to the subject for correcting a distribution of refractive indexes of the light paths (refer to the above-mentioned item (29)). The use of the correction plate makes it possible to provide a higher quality of tomographic image.

It is acceptable that the equipment main body is provided with a display unit to display the tomographic image obtained by the equipment (refer to the above-mentioned item (30)). Alternatively, it is acceptable to provide a display apparatus or a hard copying apparatus independently on the equipment.

DESCRIPTION OF THE PREFERRED EMBODIMENTS

Hereinafter, there will be described embodiments of the present invention.

Figure 1:
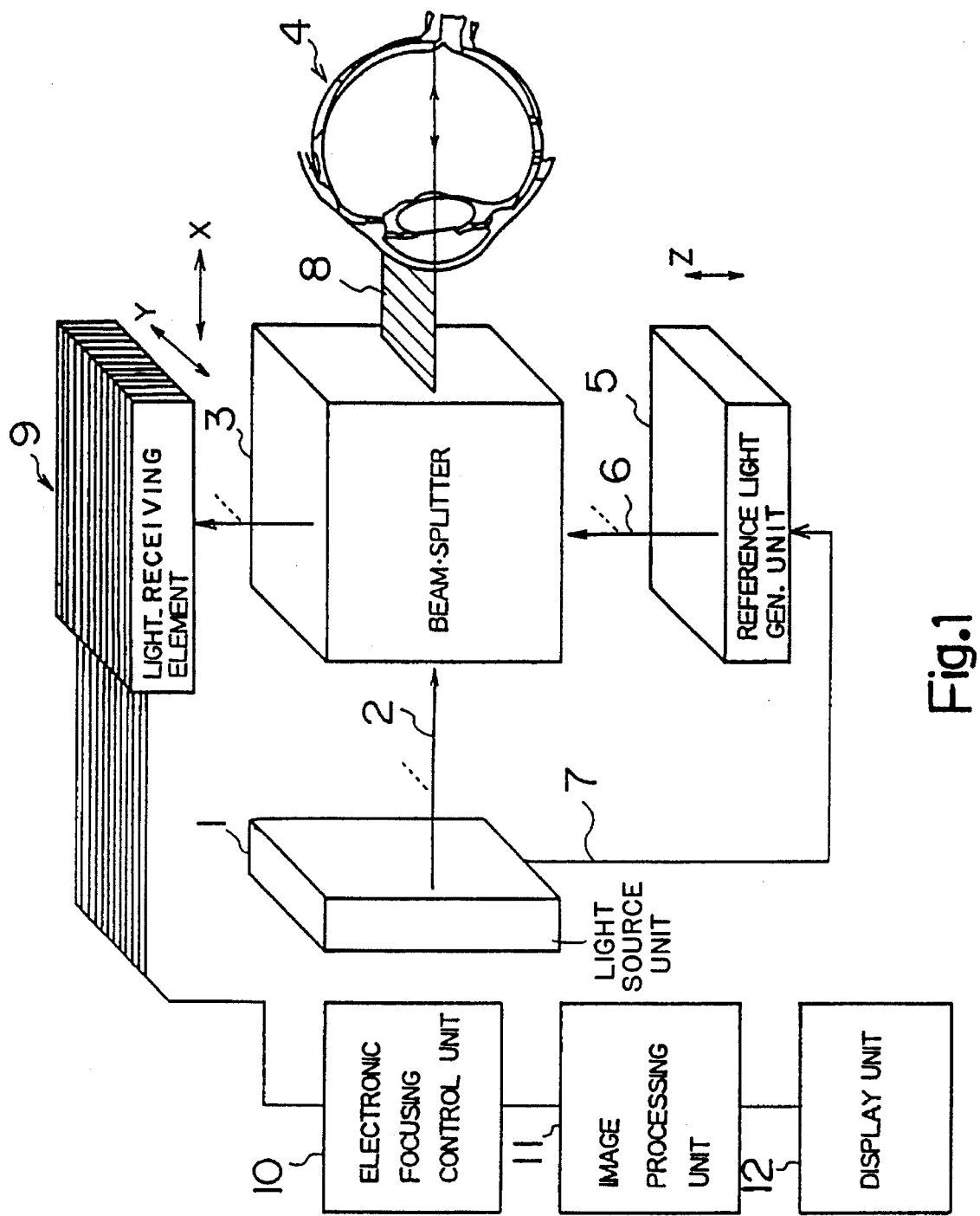
FIG. 1 is a schematic diagram showing a conceptual structure of an optical tomographic imaging equipment according to an embodiment of the present invention.

FIG. 1 is a schematic diagram showing a conceptual structure of an optical tomographic imaging equipment according to an embodiment of the present invention.

In FIG. 1, a light source unit 1 has, as a light source, an SLD (Super Luminescent Diode), an LED (Light Emitting Diode) or the like. A light wave emanating from the light source unit 1 is divided into two light waves, one of which is projected, as the first light wave 2 or an object light, through a beam splitter 3 on a measuring object 4. The object light 2 incident on the measuring object is reflected and scattered inside of the measuring object. According to the present embodiment, the light source unit 1 comprises a plurality of light sources which are arranged in the form of a one dimensional array. A scanning as to a Y-direction (scanning direction) is conducted through switching those light sources. Incidentally, according to the present embodiment, while there is exemplarily shown an eye as the measuring object 4, the measuring object 4 is not restricted to the eye.

A reference light generating unit 5 generates reference light 6 to discriminate optical signals from a desired point inside of the measuring object 4 in such a manner that the object light 2 projected on the measuring object 4 interferes with the reflected light beams returning to the beam splitter 3 through reflecting from various points on a travelling path of the object light beam inside of the measuring object 4. The reference light generating unit 5 may move in a Z-direction so as to apply to the reference light a Doppler frequency shift to produce a heterodyne signal. A two dimensional tomographic plane 8 is provided through the combination of the definition of the depth direction inside of the measuring object 4 by the reference light and the scanning by means of switching the plurality of light sources.

The reflected light from the measuring object 4 is superposed on the reference light at a reflection plane of the beam splitter 3 to interfere with each other, and then transmitted as an interference light to a light-receiving unit 9. Thus, it is possible to substantially discriminate the reflected light including optical signals from a desired point inside of the measuring object 4. The light-receiving unit 9 comprises a plurality of photo-electric elements arranged in the Y-direction. The reflected light interfered with the reference light is received by each of the photo-electric elements within a light-receiving aperture comprising a plurality of photo-electric elements which are of a part selected from among said plurality of photo-electric elements constituting the light-receiving unit 9, thereby obtaining a heterodyne signal including phase information. Each heterodyne signal derived from the associated photo-electric element is transmitted to an electronic focusing control unit 10 in which an electronic focusing control through a variable delay and an addition by electronic means is conducted to form a desired focusing.

In FIG. 1, the light-receiving unit 9 is depicted as a one dimensional array in which a plurality of photo-electric elements are arranged on a one dimensional basis in the Y-direction. In this case, the focusing control as to only the Y-direction (scanning direction) is permitted. It is noted, however, that if the photo-electric elements are of a two dimensional array, the focusing control as to both the Y-direction (scanning direction) and the X-direction (thickness direction) or (direction perpendicularly intersecting both the optical axis of the interference light incident on the photo-electric elements and the scanning direction (Y-direction)), is permitted.

With respect to the light-receiving gain at the respective light-receiving position within the selected light-receiving aperture, an apodization in a Gaussian line shape (or a Gaussian plane) taking a center of the aperture with a peak permits a preferable beam shape to be obtained. Further, if the size of the light-receiving aperture is varied in accordance with the position of the reference light generating unit 5 in the Z-direction, it is possible to obtain even beams in diameter with respect to the depth direction (Z-direction). According to the present embodiment, the light-receiving aperture is electronically scanned in the Y-direction through electronic switching.

The signals, which have been subjected to the delay and addition processing in the electronic focusing control unit 10, are transmitted to an image processing unit 11 to practice a suitable image processing. The signals which have undergone the image processing are transmitted to a display unit 12 on which a tomographic image of the measuring object 4 is displayed.

Figure 2:
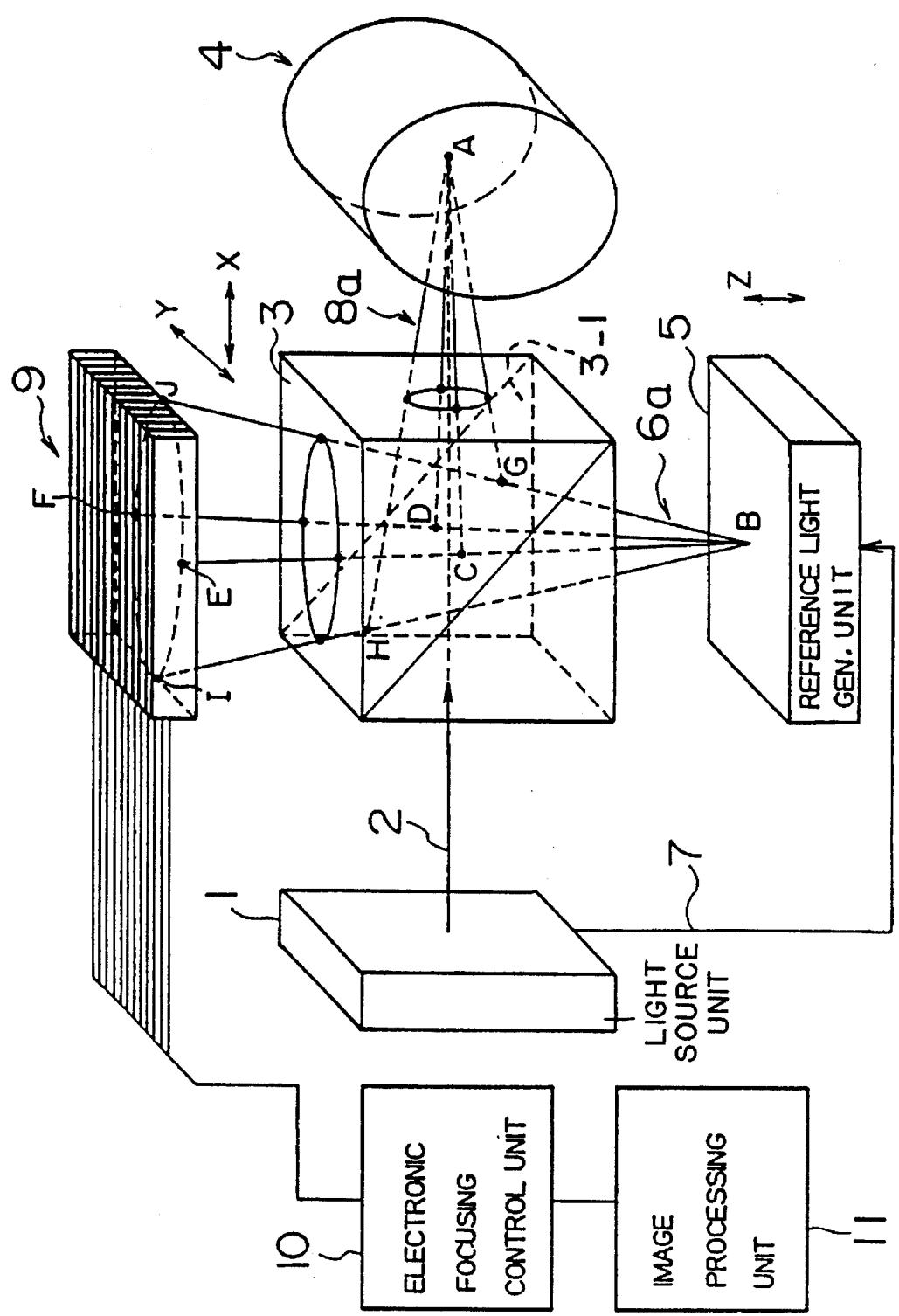
FIG. 2 is a schematic diagram showing a partially detailed structure of the optical tomographic imaging equipment according to the embodiment shown in FIG. 1.

FIG. 2 is a schematic diagram showing a partially detailed structure of the optical tomographic imaging equipment according to the embodiment shown in FIG. 1.

It is ideal that a light path 6a of the reference light from the reference light generating unit 5 toward the beam splitter 3 is equivalent to a light path which is obtained when a cone shaped light path 8a of which a top is given by a measuring point A inside of the measuring object 4, along which the reflected light from the measuring point A travels toward the beam splitter 3, is turned back at a reflection plane 3_1 of the beam splitter 3. However, it is sufficient for the light path 6a to be close to that obtained when the light path 8a of the reflected light is turned back.

The reference light from a point B of the reference light generating unit 5 toward the beam splitter 3 passes through a reflection plane HCGD of the beam splitter 3 and arrives at a plane IEJF of the light-receiving unit 9.

The reflected light from the point A of the measuring object 4 is reflected on the reflection plane HCGD of the beam splitter 3 and arrives at the plane IEJF of the light-receiving unit 9 to interfere with the reference light. Thus, it is possible to substantially discriminate the reflected light including optical signals from a desired measuring point A inside of the measuring object 4. As mentioned above, the reflected light, which has interfered with the reference light, is received in the form of the heterodyne signal having phase information by each of the photo-electric elements within a light-receiving aperture comprising a plurality of photo-electric elements which are of a part selected from among the plurality of photo-electric elements constituting the light-receiving unit 9. Each heterodyne signal derived from the associated photo-electric element is transmitted to the electronic focusing control unit 10 in which an electronic focusing control through a variable delay and an addition by electronic means is conducted to form a desired focusing.

Even if the reference light is spread up to outside of the light-receiving aperture, the effective reference light is limited by the definition of the light-receiving aperture.

Assuming that there is given a point Ai which is located at a symmetrical position for a point A with respect to the reflection plane HCGD of the beam splitter 3, a difference in the optical path between the reflected light and the reference light may be determined through comparing a light path within a solid determined by a bottom IEJF and the top Ai with a light path within a solid determined by a bottom IEJF and the top B.

Figure 3:
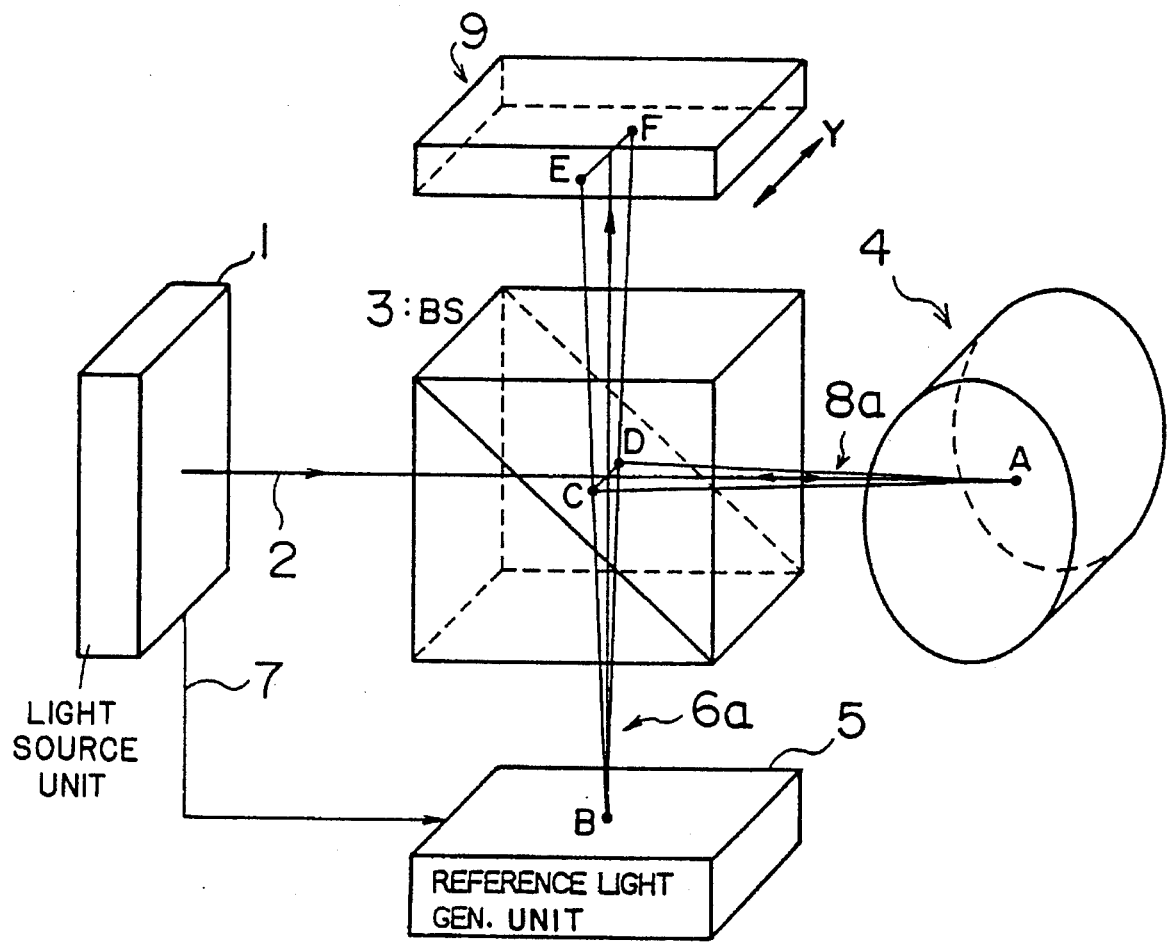
FIG. 3 is a schematic diagram showing a functional structure of the optical tomographic imaging equipment according to the embodiment shown in FIG. 1, paying attention to a light path in a scanning direction.

FIG. 3 is a schematic diagram showing a functional structure of the optical tomographic imaging equipment according to the embodiment shown in FIG. 1, paying attention to a light path in a scanning direction (a Y-direction).

The reference light from a point B of the reference light generating unit 5 toward the beam splitter 3 passes through a reflection plane CD of the beam splitter 3 and arrives at a plane EF of the light-receiving unit 9.

The reflected light from the point A of the measuring object 4 is reflected on the reflection plane CD of the beam splitter 3 and arrives at a plane EF of the light-receiving unit 9 to interfere with the reference light. Thus, it is possible to substantially discriminate the reflected light including optical signals from a desired measuring point A inside of the measuring object 4. The reflected light, which has interfered with the reference light, is received in the form of the heterodyne signal having phase information by each of the photo-electric elements within a light-receiving aperture comprising a plurality of photo-electric elements which are of a part selected from among the plurality of photo-electric elements constituting the light-receiving unit 9. Each heterodyne signal derived from the associated photo-electric element is subjected to an electronic focusing control through a variable delay by electronic means to form a desired focusing. According to the arrangement shown in FIG. 3, the focusing control with respect to the scanning direction (Y-direction) is implemented through an electronic focusing control with respect to the EF direction of the light-receiving unit 9. Even if the reference light is spread up to outside of the light-receiving aperture, the effective reference light is limited by the definition of the light-receiving aperture.

Assuming that there is given a point Ai which is located at a symmetrical position for a point A with respect to the reflection plane CD of the beam splitter 3, a difference in the optical path between the reflected light and the reference light may be determined by comparing a light path within a triangle AiEF with a light path within a triangle BEF.

Figure 4:
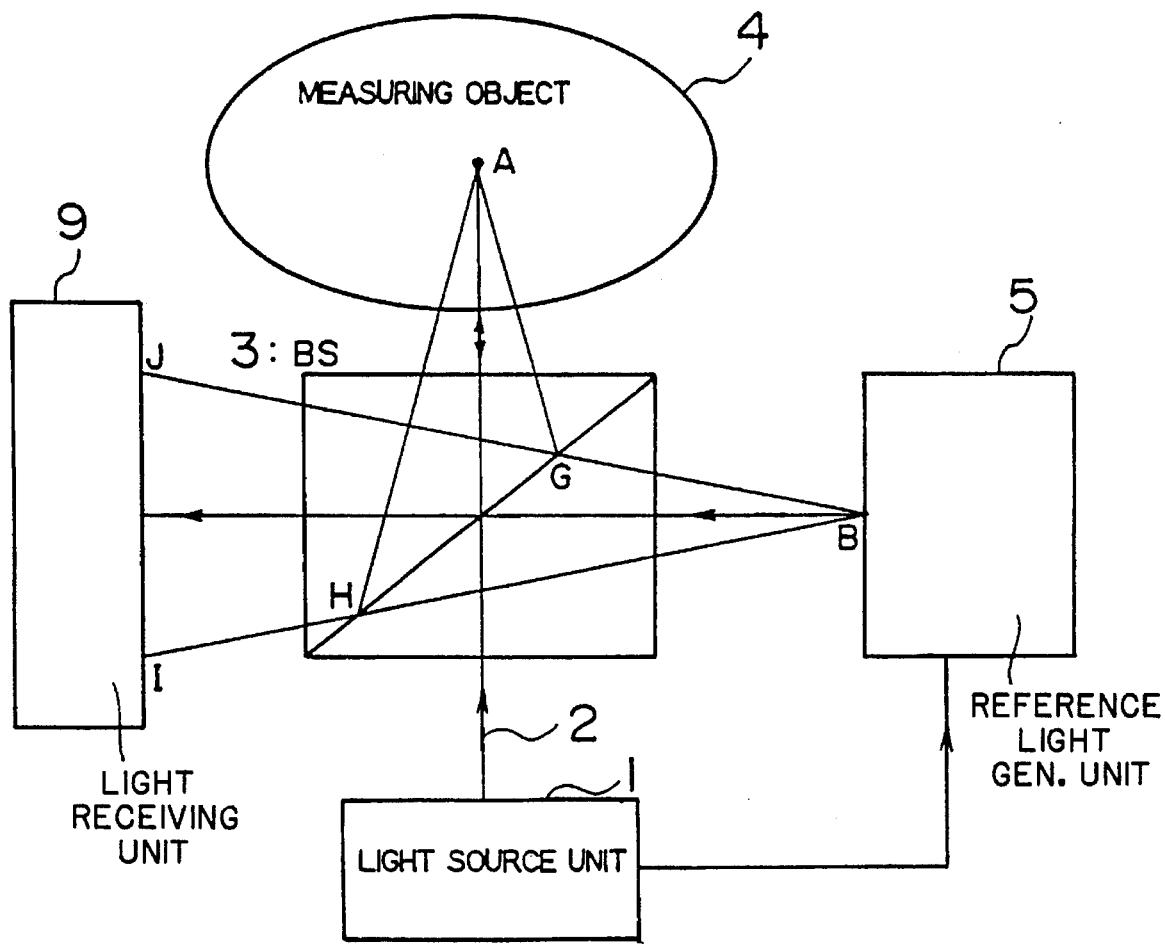
FIG. 4 is a schematic diagram showing a functional structure of the optical tomographic imaging equipment according to the embodiment shown in FIG. 1, paying attention to a light path in a thickness direction.

FIG. 4 is a schematic diagram showing a functional structure of the optical tomographic imaging equipment according to the embodiment shown in FIG. 1, paying attention to a light path in a thickness direction (a X-direction in FIG. 1).

The reference light, projected from a point B of the reference light generating unit 5 toward the beam splitter 3, passes through a reflection plane HG of the beam splitter 3 and arrives at a plane IJ of the light-receiving unit 9.

The reflected light from the point A of the measuring object 4 is reflected on the reflection plane HG of the beam splitter 3 and arrives at a plane IJ of the light-receiving unit 9 to interfere with the reference light. Thus, it is possible to substantially discriminate the reflected light including optical signals from a desired measuring point A inside of the measuring object 4. If the light-receiving unit 9 is provided with a two dimensional array, the reflected light, which has interfered with the reference light, is received in the form of the heterodyne signal having phase information by each of the photo-electric elements within a light-receiving aperture comprising a plurality of photo-electric elements which are of a part selected from among the plurality of photo-electric elements constituting the light-receiving unit 9. Each heterodyne signal derived from the associated photo-electric element is subjected to an electronic focusing control through a variable delay by electronic means to form a desired focusing. In such a case, the focusing control with respect to the thickness direction is implemented through an electronic focusing control with respect to the IJ direction of the light-receiving unit 9. However, according to the embodiment shown in FIG. 1, the light-receiving unit 9 is provided with a one dimensional array, and thus the electronic focusing control with respect to the thickness direction is not implemented. Even if the reference light is spread up to outside of the light-receiving aperture, the effective reference light is limited by the definition of the light-receiving aperture IJ.

Assuming that there is given a point Ai which is located at a symmetrical position for a point A with respect to the reflection plane HG of the beam splitter 3, a difference in the optical path between the reflected light and the reference light may be determined by comparing a light path within a triangle AiIJ with a light path within a triangle BIJ.

From the above-mentioned matter, it is apparent that with respect to both the scanning direction and the thickness direction, there is simply a difference therebetween in the location of the boundary due to the reflection plane of the beam splitter 3, and it is possible to deal with the electronic focusing control and the difference of optical path in the same fashion for any of those directions. Consequently, in general, it is possible to treat the electronic focusing control and the difference in the optical path in the same fashion for any of those directions, but there is merely a difference in the location of the boundary due to the reflection plane of the beam splitter 3, between the scanning direction (Y-direction) and the thickness direction (X-direction) with respect to the synthesis from those directions.

Figure 5:
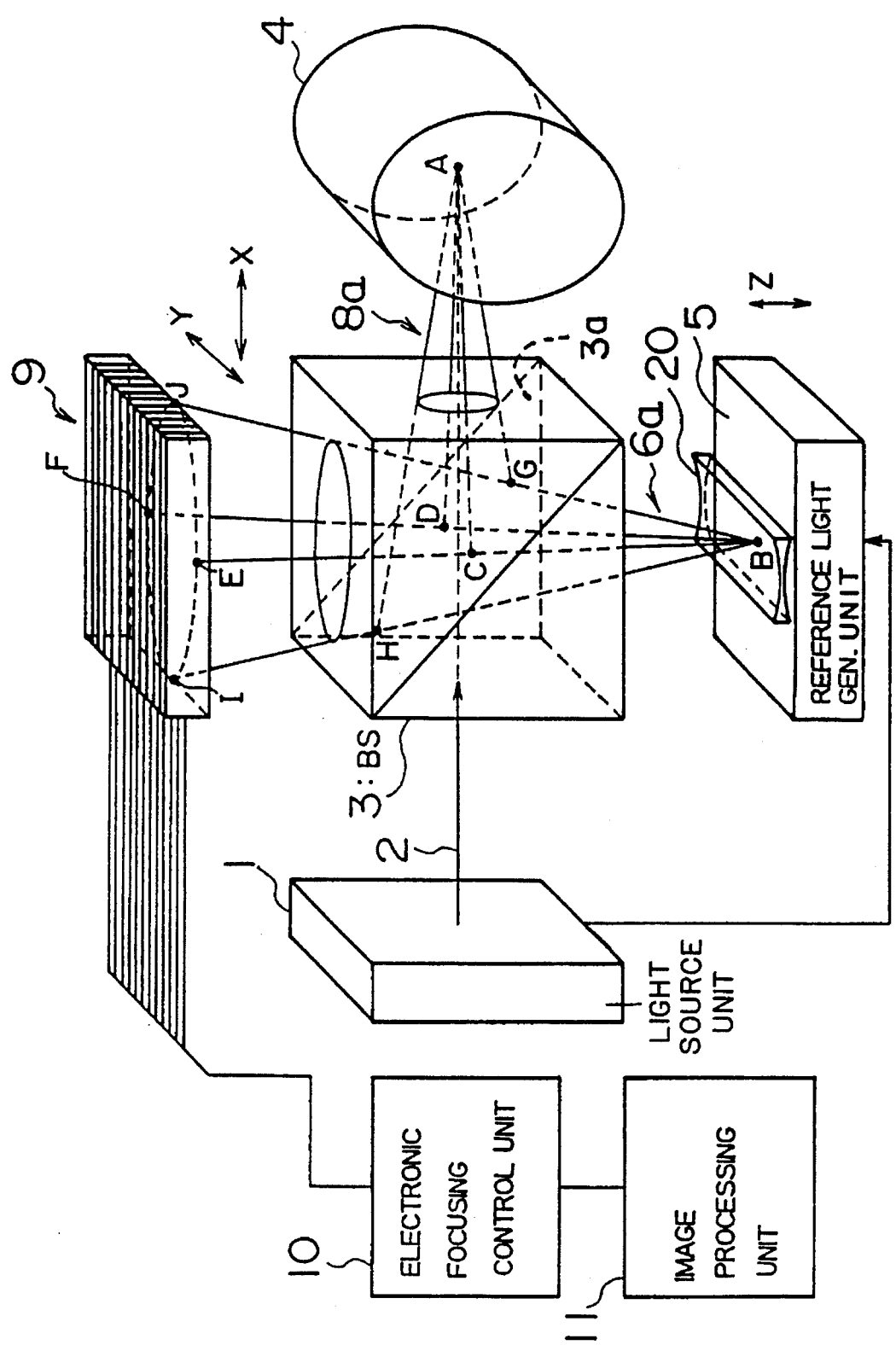
FIG. 5 is a schematic diagram showing a partially detailed structure of an optical tomographic imaging equipment in which a focusing is controlled by a cylindrical lens having a thickness distribution with respect to only the thickness direction, the cylindrical lens being fixed on a reference light generating unit and movable together with the same.

FIG. 5 is a schematic diagram showing a partially detailed structure of optical tomographic imaging equipment.

In FIG. 5, a light-receiving unit 9 comprises a one dimensional array in which a plurality of photo-electric elements are arranged on a one dimensional basis in the scanning direction (Y-direction). A focusing control is performed electronically with respect to the scanning direction (Y-direction). On the other hand, the focusing control is performed, with respect to the thickness direction (X-direction), by a cylindrical lens having a thickness distribution with respect to only the thickness direction (X-direction), the cylindrical lens being fixed on a reference light generating unit 5 and movable together with the same in a Z-direction.

In FIG. 5, a light source unit 1 has, as a light source, a SLD (Super Luminescent Diode), a LED (Light Emitting Diode) or the like. A light wave emanating from the light source unit 1 is projected, as an object light 2, through a beam splitter 3 on a measuring object 4. The object light 2 incident on the measuring object 4 is reflected and scattered inside of the measuring object 4. According to the present embodiment, the light source unit 1 comprises a plurality of light sources which are arranged in the form of a one dimensional array. A scanning as to a Y-direction (scanning direction) is conducted through switching those light sources.

The reference light generating unit 5 generates reference light to discriminate optical signals from a desired measuring point A inside of the measuring object 4 in such a manner that the object light 2 projected on the measuring object 4 interferes with the reflected light beams returning to the beam splitter 3 through reflection from various points on a travelling path of the object light beam inside of the measuring object 4. The reference light generating unit 5 may move in the Z-direction so as to apply to the reference light a Doppler frequency shift to produce a heterodyne signal. It is ideal that a light path 6a of the reference light from the reference generating unit 5 toward the beam splitter 3 is equivalent to a light path which is obtained when a cone shaped light path 8a of which a top is given by a measuring point A inside of the measuring object 4, along which the reflected light from the measuring point A travels toward the beam splitter 3, is turned back at a reflection plane 3a of the beam splitter 3. However, it is sufficient for the light path 6a to be close to that obtained when the light path 8a of the reflected light is turned back.

The reference light emitted from a point B of the reference light generating unit 5 passes through a reflection plane HCGD of the beam splitter 3 and arrives at a plane IEJF of the light-receiving unit 9.

The reflected light from the point A of the measuring object 4 is reflected on the reflection plane HCGD of the beam splitter 3 and arrives at a plane IEJF of the light-receiving unit 9 to interfere with the reference light. Thus, it is possible to substantially discriminate the reflected light including optical signals from a desired measuring point A inside of the measuring object 4. As mentioned above, the reflected light, which has interfered with the reference light, is received in the form of the heterodyne signal having phase information by each of the photo-electric elements within a light-receiving aperture comprising a plurality of photo-electric elements which are of a part selected from among the plurality of photo-electric elements constituting a large aperture array of the light-receiving unit 9. Each heterodyne signal derived from the associated photo-electric element is subjected to an electronic focusing control through a variable delay by electronic means to form a desired focusing.

With respect to the thickness direction (X-direction), the focusing control is performed by a cylindrical lens 20 having a thickness distribution with respect to only the thickness direction, the cylindrical lens 20 being fixed on a reference light generating unit 5 and movable together with the same in the Z-direction. While FIG. 5 depicts a piece of cylindrical lens 20, it is of course acceptable to adopt a cylindrical lens in combination with two or more lens.

Even if the reference light is spread up to outside of the light-receiving aperture, the effective reference light is limited by the definition of the light-receiving aperture.

Figure 6:
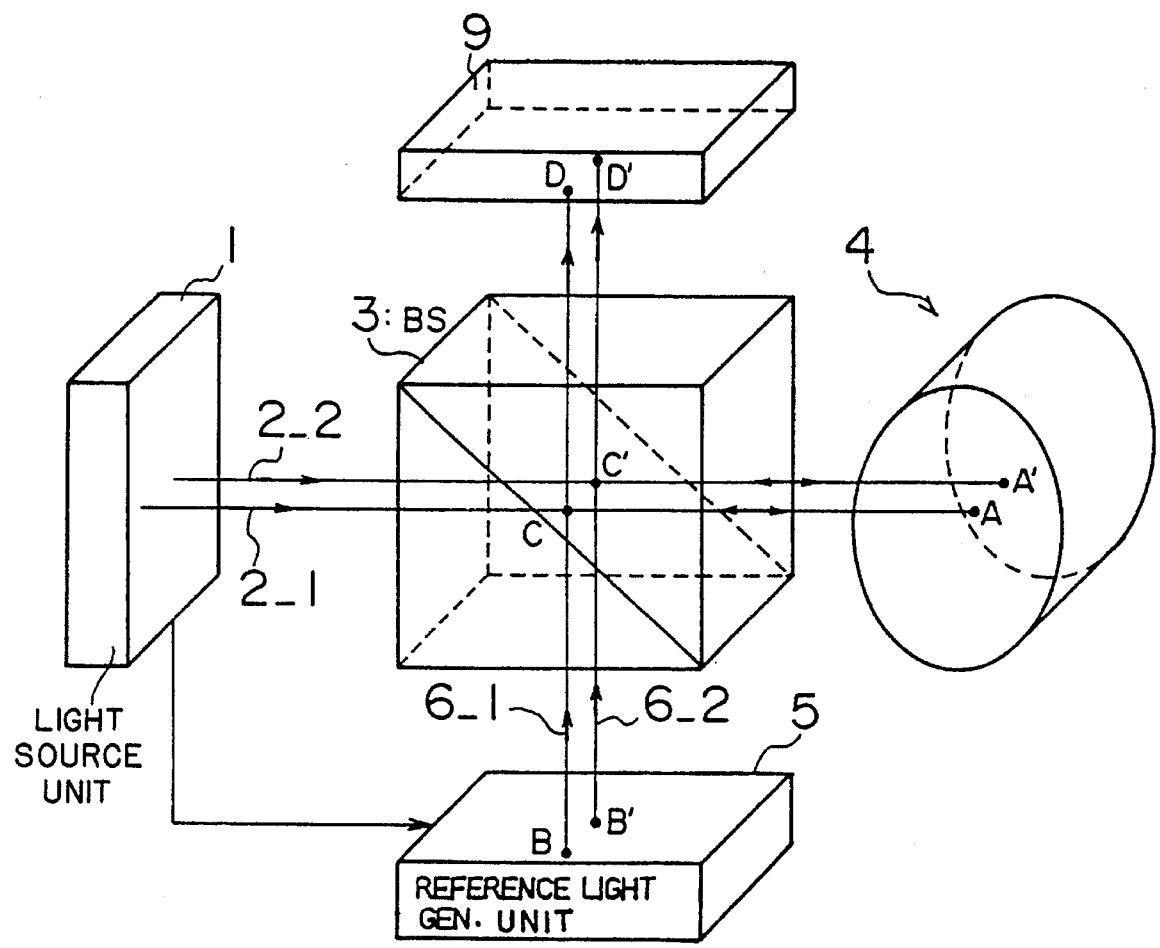
FIG. 6 is a schematic diagram showing a functional structure of an optical tomographic imaging equipment in which a plurality of object light beams are simultaneously emitted from at least two points spaced to such an extent that the object light emitted from each point do not interfere, and then be simultaneously received.

FIG. 6 is a schematic diagram showing a functional structure of optical tomographic imaging equipment in which a plurality of object light beams are simultaneously emitted from at least two points spaced to such an extent that the object light emitted from each point do not interfere, and then be simultaneously received.

The reference light beams 6_1 and 6_2, which are emitted from points B and B' of the reference light generating unit 5, respectively, pass through points C and C' on a reflection plane of the beam splitter 3 and arrive at points D and D' of the light-receiving unit 9, respectively.

The reflected light beams from the points A and A' of the measuring object 4 are reflected on the points C and C' on the reflection plane of the beam splitter 3 and arrive at the points D and D' of the light-receiving unit 9 to interfere with the reference light beams 6_1 and 6_2, respectively. Thus, it is possible to substantially discriminate the reflected light beams including optical signals from desired measuring points A and A' inside of the measuring object 4. Each of the reflected light beams, which has interfered with the associated reference light beam, is received in the form of the heterodyne signal having phase information by each of the photo-electric elements within a light-receiving aperture comprising a plurality of photo-electric elements which are of a part selected from among the plurality of photo-electric elements constituting a large aperture array of the light-receiving unit 9. Each of the heterodyne signals derived from the associated photo-electric elements is subjected to an electronic focusing control through a variable delay by electronic means to discriminate the desired measuring points A and A'. With respect to those measuring points A and A', there are selected at least two points spaced to such an extent that the object light beams and the reference light beams from the points do not interfere with each other. In this case, since there is formed a plurality of pairs each comprising an object light beam and a reference light beam through mutually different light sources, there is no need to consider an interference between the mutually different light sources. Further, even if the reference light beams are overlapped each other, it is possible to separate those to some extent in accordance with the electronic focusing control.

While FIG. 6 depicts only the central light paths, indeed, similar to FIG. 2, a cone shaped beam is dealt with. Further, while FIG. 6 shows an example in which a scanning line-to-line interval or a width between the scanning lines is divided into two segments, in general, the scanning line-to-line interval is divided into N segments, and N pieces of light beam are simultaneously emitted from scanning line points spaced at intervals of 1/N of the scanning line-to-line width, and then are simultaneously received. This system may be advantageously adopted in case of a broad scanning line-to-line width.

Figure 7:
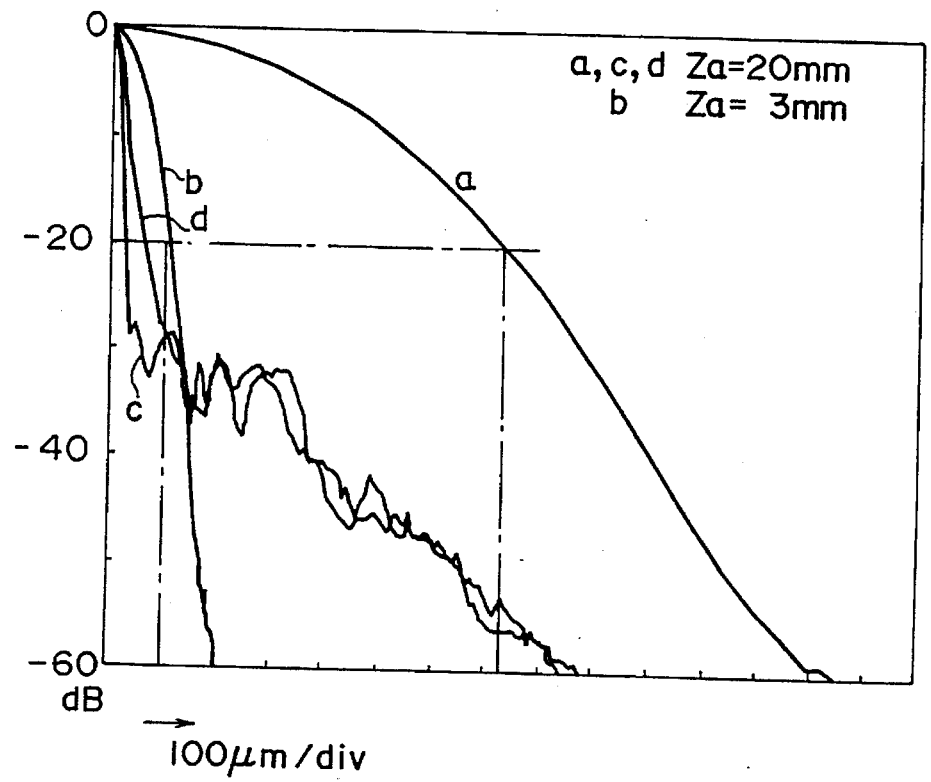
FIG. 7 is an illustration showing a simulation result as to a directivity of the lateral direction (direction perpendicularly intersecting to the optical axis) when the reflected light from inside of the subject is received.

FIG. 7 is an illustration showing a simulation result as to a directivity of the lateral direction (direction perpendicularly intersecting to the optical axis) when the reflected light from inside of the subject is received. FIG. 7 depicts only half the right and with the left end in the center (optical axis) of a beam.

Graphs a and b illustrate the simulation results in a case where no electronic focusing control is conducted, assuming that light emitted from an optical fiber having 24 μm of aperture is projected as the object light onto the inside of a measuring object, and light beams reflected at the locations of depths 20 mm and 3 mm within the measuring object are incident on the optical fiber. According to the graph b assuming that the light beam is reflected at the depth 3 mm, there is provided a spread, about 2×100 μm, at −20 dB. On the other hand, according to the graph, assuming that the light beam is reflected at the depth 20 mm, there is provided more than six times the spread concerning the depth 3 mm.

Consequently, it would be difficult to obtain sufficient resolution in accordance with a scheme in which optical fibers are spaced at intervals of, for example, several tens μm, and a scanning as to the lateral direction is conducted only through switching of the optical fiber.

Graphs c and d illustrate, in a similar fashion as in the case of graph a, the simulation result in a case where assuming that an optical fiber having 24 μm of aperture is used and the light beam is reflected at the depth 20 mm, a reflected light emitted from the optical fiber is interfered with the reference light, and a large aperture (several mm) of array shaped photo-electric elements is used to receive the light. Graph c is concerned with a case where the electronic focusing control is conducted in such a manner that an aberration in the optical path between the reference light and the reflected light is completely adjusted with respect to both the parts involved in an integral multiple of the wave length λ of the light source and the fraction parts less than the wave length λ, in other words, to provide a complete coincidence of the origin 0 in FIG. 27. As seen from the figure, a sufficiently fine beam is produced.

Graph d illustrates the simulation result in a case where the electronic focusing control is conducted in such a manner that an aberration in the optical path between the reference light and the reflected light is adjusted with respect to only the fraction parts less than the wave length λ of the light source, omitting the parts involved in an integral multiple of the wave length λ. In other words, according to such an electronic focusing control, there is provided such a control that a coincidence of only the phase of the carrier is implemented, ignoring the aberration of the origin 0 in FIG. 27. Even in this case, also, it is possible to attain a remarkably well focused effect.

Figure 8:
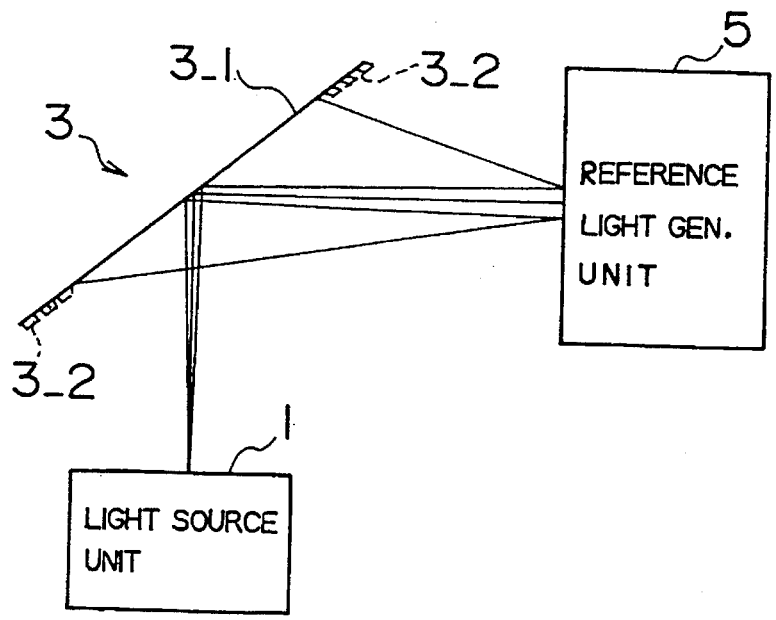
FIG. 8 is a diagram useful for explanation of a light source unit and a reference light generating unit by way of example.

FIG. 8 is a diagram useful for explanation of a light source unit 1 and a reference light generating unit 5 by way of example.

It is acceptable that the reference light generating unit 5 is simply a movable mirror, and thus it has an advantageous point in that the structure is simple. A Doppler frequency is determined in accordance with a travelling speed of the movable mirror. The movable mirror is designed in such a manner that in order to provide a light scattering characteristic, the movable mirror has a suitable surface roughness which is finer than a wave length of the light source so as to induce a slight diffuse reflection. The light source unit 1 comprises a plurality of optical fibers each having a predetermined diameter, and which are arranged at regular intervals in a vertical direction with respect to the sheet of FIG. 8. The optical fibers are each equipped with a light emitting element such as an SLD (Super Luminescent Diode), a LED (Light Emitting Diode) or the like at their one end. The scanning is performed through switching those light emitting elements.

It is preferable to set up a mask 3_2 to eliminate redundant light at the reference light incident end of the reflection plane 3_1 of the beam splitter 3. It is acceptable that the mask 3_2 is set up at the equivalent position on the surface of the beam splitter 3 instead of the above-referenced position.

Based on the optical axis as the center of the light path, a maximum interference occurs at a position (corresponding to the origin in FIG. 27) which is a reflecting position within the measuring object 4 (refer to FIG. 2) with which the number of waves of light incident on the light path starting from the light source through the reference light generating unit 5 to the reflection plane 3_1 of the beam splitter 3 becomes equal to the number of waves of light incident on the light path starting from the light source, passing through the reflection plane of the beam splitter 3, being scattered and reflected from the inside of the measuring object 4 and up to turning back to the reflection plane of the beam splitter 3.

Figure 9:
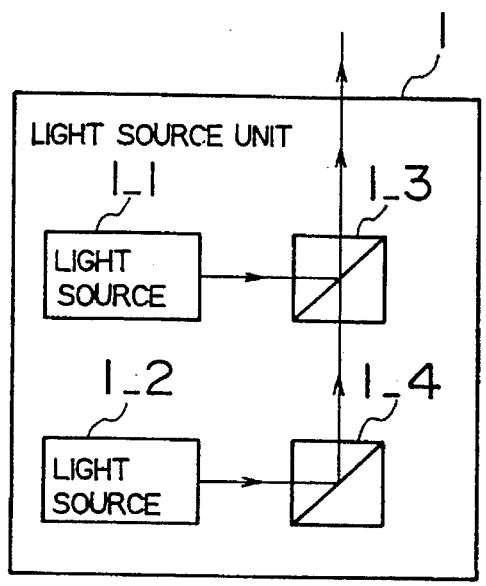
FIG. 9 is a diagram useful for explanation of a light source unit by way of example.

FIG. 9 is a diagram useful for explanation of a light source unit by way of example.

FIG. 9 is an example in which a light source unit 1 has no optical fiber. The light source unit 1 includes upper and lower stages of light sources 1_1 and 1_2. In FIG. 9, there are provided a plurality of light sources 1_1 which are arranged in a line in the vertical direction with respect to the sheet of the figure. Likewise, a plurality of light sources 1_2 are arranged in a line in the vertical direction with respect to the sheet of the figure. The light source unit 1 further includes upper and lower stages of beam splitters 1_3 and 1_4. It is so arranged that the light sources may be disposed at intervals corresponding to the number of stages of the beam splitters 1_3 and 1_4 in the vertical direction with respect to the sheet of the figure. The beam splitters 1_3 and 1_4 each have a scanning width of length in the vertical direction with respect to the sheet of the figure.

The above-mentioned structure is effective for the light source having an array structure constituted of a plurality of light emitting elements.

Figure 10:
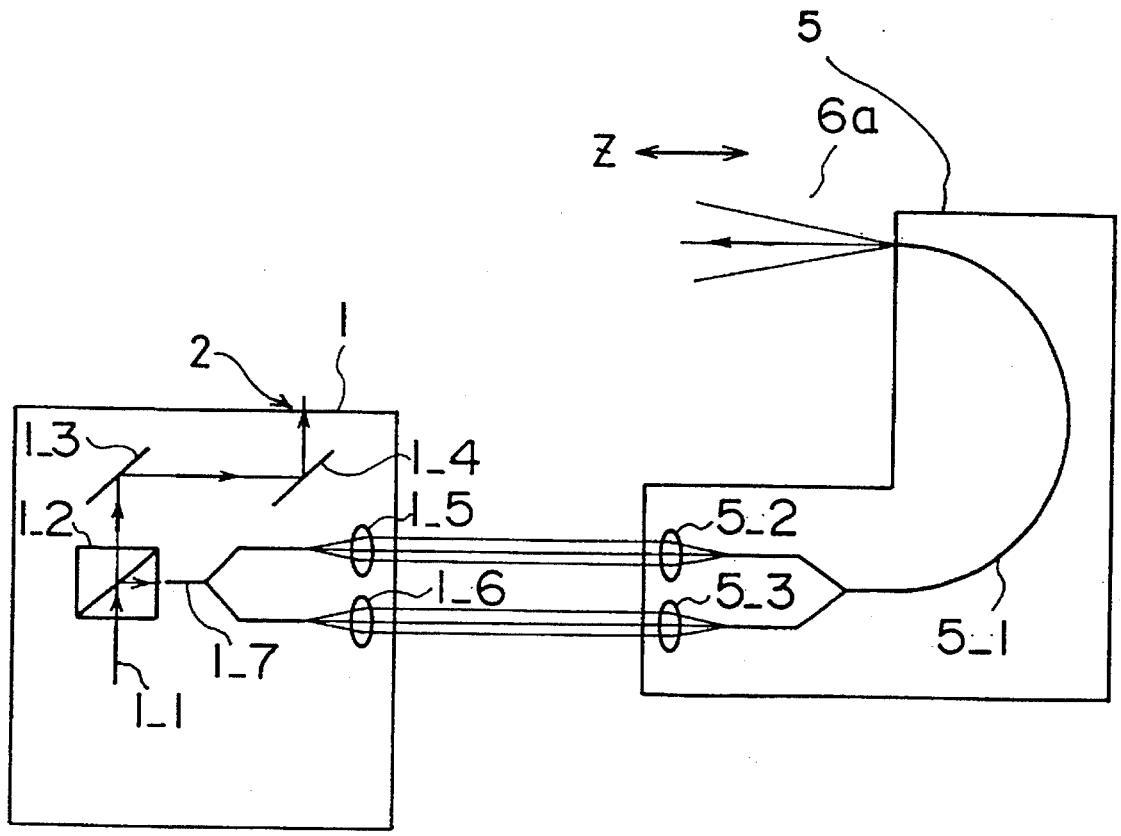
FIG. 10 is a diagram useful for explanation of a light source unit and a reference light generating unit according to another example.

FIG. 10 is a diagram useful for explanation of a light source unit and a reference light generating unit according to another example.

A light path 6a of a reference light emitted from an optical fiber 5_1 mounted on a reference light generating unit 5 is very close to a cone shaped light path of which a top is given by a measuring point A inside of the measuring object 4. The reference light generating unit 5 is moved in a Z-direction, so that the reference light emitted from the optical fiber 5_1 is subjected to a Doppler frequency shift according to the moving velocity of the reference light generating unit 5.

The light source unit 1 comprises a plurality of optical fibers 1_1 each having a predetermined diameter, and which are arranged at regular intervals in a vertical direction with respect to the sheet of FIG. 10. The optical fibers 1_1 are each equipped with a light emitting element such as an SLD (Super Luminescent Diode), an LED (Light Emitting Diode) or the like at their one end not illustrated. The scanning is performed through switching those light emitting elements. The light emitted from the optical fiber 1_1 enters a beam splitter 1_2 and is divided into the second light wave travelling via an optical fiber 1_7, and lenses 1_5 and 1_6 to the reference light generating unit 5, and object light to be emitted via mirrors 1_3 and 1_4 from the light source unit 1. The mirrors 1_3 and 1_4 serve to regulate a difference in the optical path between the light path at the reference light generating unit side and the light path at the measuring object side, starting from the beam splitter 1_2. The object light 2 emitted from the light source unit 1 is incident on the beam splitter 3 shown in FIG. 1.

In FIG. 10, a plurality of optical fibers 1_7, which are arranged at a vertical direction with respect to the sheet of FIG. 10, each have two separated output terminals of the optical fibers 1_7 mutually checkered up and down, in order to permit the arrangement intervals to be spread. Of course, an increment of the number of stages in the up and down direction permits the arrangement interval to be spread further apart. The second light wave emitted from the optical fiber 1_7 is spread in beam width through the lenses 1_5 and 1_6, and the beams derived from the lenses 1_5 and 1_6 are transmitted in the form of a collimated beam to the reference light generating unit 5, maintaining the spread beam width. It is preferable to provide, at the respective ends of the light source unit 1 and the reference light generating unit 5, a corresponding nesting shield plate for separating the collimated beam-to-beam from each other.

In the reference light generating unit 5, the beams are converged through lenses 5_2 and 5_3 and then supplied to an optical fiber 5_1. At the other end of the optical fiber 5_1, the arrangement interval is set the same as the optical fiber 1_1, so that the reference light is emitted from the other end terminal. This arrangement makes it possible to implement an emission terminal of the reference light with a very fine beam which is determined by the diameter of the optical fiber.

Based on the optical axis as the center of the light path, a maximum interference occurs at a position which is a reflecting position within the measuring object 4 with which the number of waves of light incident on the light path starting from the light source through the reference light generating unit 5 to the reflection plane of the beam splitter 3 shown in FIG. 1 becomes equal to the number of waves of light incident on the light path starting from the light source, passing through the reflection plane of the beam splitter 3, being scattered and reflected from the inside of the measuring object 4 and up to turning back to the reflection plane of the beam splitter 3.

Figure 11:
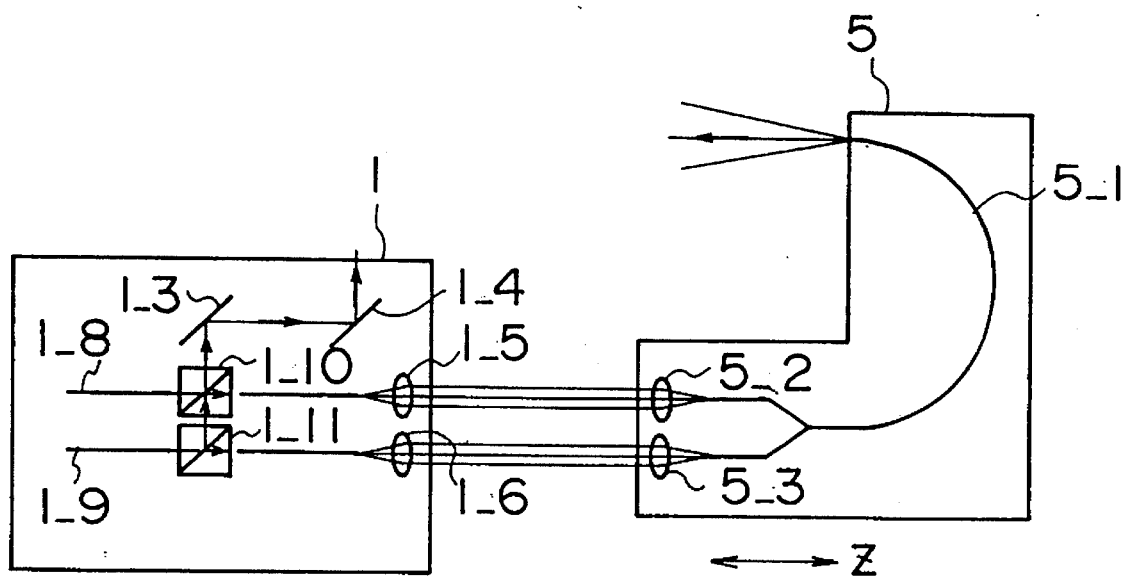
FIG. 11 is a diagram useful for explanation of a light source unit and a reference light generating unit according to still another example.

FIG. 11 is a diagram useful for explanation of a light source unit and a reference light generating unit according to still another example. In FIG. 11, similar to FIG. 10, the light source unit 1 comprises a plurality of optical fibers 1_8 and 1_9 each having a predetermined diameter, which are arranged at regular intervals in a vertical direction with respect to the sheet of FIG. 11, respectively. The optical fibers 1_8 are each equipped with a light emitting element such as an SLD (Super Luminescent Diode), an LED (Light Emitting Diode) or the like at their one end but which are not illustrated. Also, with respect to the optical fibers 1_9, they are the same as the optical fibers 1_8. The scanning is performed through switching those light emitting elements. An arrangement of two stages of the optical fibers 1_8 and 1_9 as shown in FIG. 11 permits arrangement intervals of the optical fibers to spread twice as long as that of the single stage on each stage.

The light introduced by the optical fiber 1_9 is divided by a beam splitter 1_11 into the second light wave travelling to the right hand of FIG. 11 and the object light 2 travelling upwards. The object light 2 passes through a beam splitter 1_10 and advances further upwards in FIG. 11.

The light introduced by the optical fiber 1_8 is divided by a beam splitter 1_10 into the second light wave travelling to the right hand of FIG. 11 and the light travelling upwards. The beam splitters 1_10 and 1_11 each have a length of a scanning width in the vertical direction with respect to the sheet of the figure. The other arrangements are the same as that of FIG. 10. A difference in the optical path due to the location of the beam splitters 1_10 and 1_11 with respect to the up and down location relations can be corrected in the reference light generating unit 5.

Of course, an increment of the number of stages of the beam splitters in the up and down direction permits the arrangement interval to be spread further apart.

Figure 12:
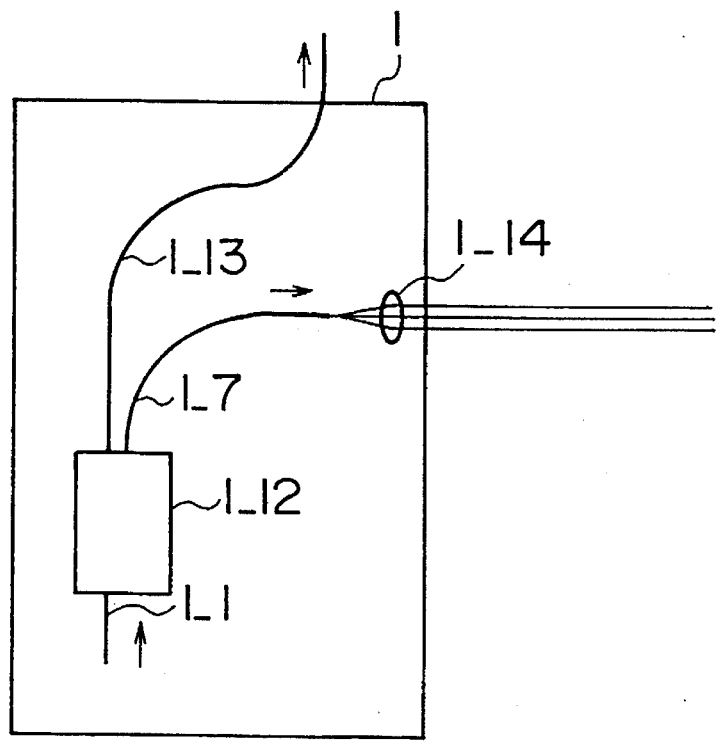
FIG. 12 is a diagram useful for explanation of a light source unit according to still another example.

FIG. 12 is a diagram useful for explanation of a light source unit according to still another example. The reference light generating unit 5 is the same as that in FIG. 10 in structure. FIG. 12 exemplarily shows the light source unit 1 constituting of fiber-couplers 1_12. This arrangement results in an advantage that a disposition of parts between the fiber-couplers 1_12 and the light emitting elements (not illustrated) may be optionally selected.

In FIG. 12, the light source unit 1 comprises a plurality of fiber-couplers 1_12 arranged at regular or irregular intervals in a vertical direction with respect to the sheet of FIG. 12, and a plurality of optical fibers 1_1, each being equipped with a light emitting element such as an SLD (Super Luminescent Diode), an LED (Light Emitting Diode) or the like at their one end but not illustrated. The optical fibers 1_1 are also arranged in a vertical direction with respect to the sheet of FIG. 12. The scanning is performed through switching those light emitting elements. The light introduced by the optical fiber 1_1 enters the fiber-coupler 1_12 and is divided into a reference light use optical fiber 1_7 and an object light use optical fiber 1_13. The terminals at the side of the beam splitter 3 (refer to FIG. 1), each of which is associated with the respective object light use optical fiber 1_13, are arranged at regular intervals in a vertical direction with respect to the sheet of FIG. 12.

In FIG. 12, it is acceptable that the plurality of reference light use optical fibers 1_7, which are arranged at a vertical direction with respect to the sheet of FIG. 12, have their associated output terminals of the reference light generating unit side mutually checkered up and down over a plurality of stages, in order to permit the arrangement intervals of the reference light use optical fibers 1_7 to be spread. The second light wave emitted from the optical fiber 1_7 is spread in beam width by the lens 1_14, and the beam derived from the lens 1_14 is transmitted in the form of a collimated beam to the reference light generating unit 5, maintaining the spread beam width. It is preferable to provide at each of the ends of the light source unit 1 and the reference light generating unit 5 a respective nesting shield plate for separating the collimated beam-to-beam from each other.

It is possible to set up an equivalence between a sum of a length of the reference light use optical fiber 1_7 from the output terminal of the fiber-coupler 1_12 of the light source unit 1 and a length of the optical fiber within the reference light generating unit 5, and a length of the object light use optical fiber 1_13. An implementation of such an equivalence makes it possible to suppress an influence of a refractive index of the optical fiber. This scheme is effective in a case where a minimum beam at the reference light side is of a sufficiently fine size, and in addition, a refractive index of the measuring object 4 is close to that of the atmosphere.

Figure 13:
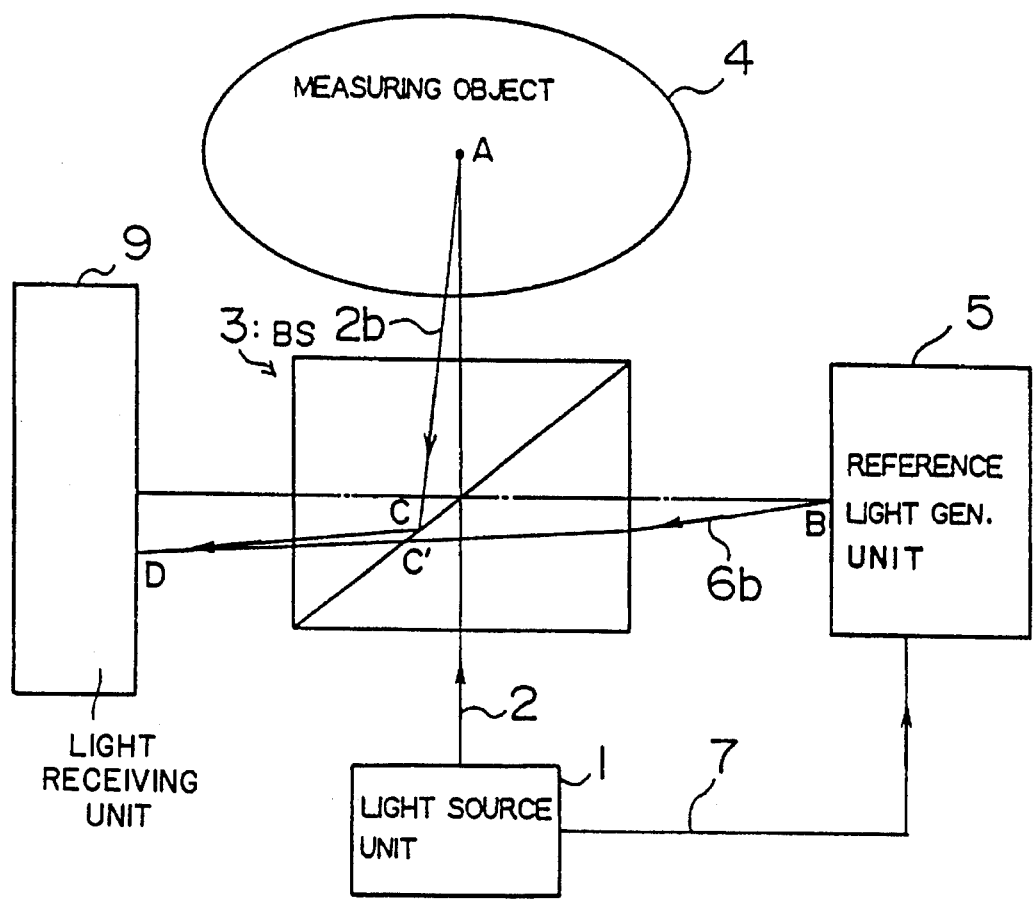
FIG. 13 is a diagram useful for explanation of characteristics of signals based on a beam incident upon a light-receiving unit via a predetermined light path in the optical tomographic imaging equipment according to the embodiment shown in FIG. 1.

FIG. 13 is a diagram useful for explanation of characteristics of signals based on a beam incident upon a light-receiving unit 9 via a predetermined light path in the optical tomographic imaging equipment according to the embodiment shown in FIG. 1.

Assuming that an origin 0 (not illustrated) is defined as a point at which a light path is branched into two ways, first way being a light path along which light emitted from a light source mounted on a light source unit 1 travels toward a reference light generating unit 5, and another way being a light path along which the light emitted from the light source mounted on the light source unit 1 travels toward a beam splitter (BS) 3; points within a reflection plane of the beam splitter 3 are given by C and C' as shown in the figure; it is supposed that reference light is emitted from the reference light generating unit 5 via an optical path 6b through the point C' to a point D; it is supposed that reflected light passing through the beam splitter 3 and reflected on a point A of a measuring object 4 passes via a light path 2b through the point C to the point D; W denotes an angular frequency; and t denotes a time base, the reflected light being represented by:

$$a1 \cdot \sin(Wt+P1)$$

where a1 denotes an amplitude, and P1 denotes a phase shift, at t=0, due to an optical path length from the origin 0 up to the point D.

The reference light is represented by:

$$a \cdot \sin(Wt+P-\epsilon t)$$

where a denotes an amplitude, P denotes a phase shift, at t=0, due to an optical path length from the origin 0 up to the point D, and $\epsilon$ denotes a Doppler shift due to the fact that the reference light generating unit 5 is moved at the velocity (v), when a wavelength of a center frequency of the light source is expressed by $\lambda$, $\epsilon = 2\pi(2v)/\lambda$.

In the light-receiving unit 9, there is detected a square of an interference light in which the above-noted reference light and reflected light are superposed on each other. Therefore, if the light-receiving signal is expressed by I(t), assuming that P1=P+p (p: difference in phase), I(t) is represented by the the following equation:

$$\begin{aligned} I(t) &= [a1 \cdot \sin(Wt+P1) + \\ &\quad a \cdot \sin(Wt+P-\epsilon t)]^2 \\ &= (a1^2 + a^2)/2 + \\ &\quad [G \cdot \sin(2Wt+2P+\Phi)]/2 + \\ &\quad a1 \cdot a \cdot [\cos(p+\epsilon t) - \\ &\quad \cos(2Wt+2P+p-\epsilon t)] \end{aligned}$$

where $$G^2 = a1^4 + a^4 + 2a1^2 a^2 \cos(2p + 2\epsilon t)$$

$$\tan(\Phi) = [-a1^2 \cos(2p) - a^2 \cos(2\epsilon t)] / [a1^2 \sin(2p) - a^2 \sin(2\epsilon t)].$$

Incidentally, since components of a frequency of light are subjected to filtering by the photo-electric elements of the light-receiving unit 9, I(t) is represented as follows:

$$I(t)=(a1^2+a^2)/2+a1.a.[\cos(p+\epsilon t)].$$

Further, removing a DC component, $$I(t)=a1.a.[\cos(p+\epsilon t)].$$

Figure 27:
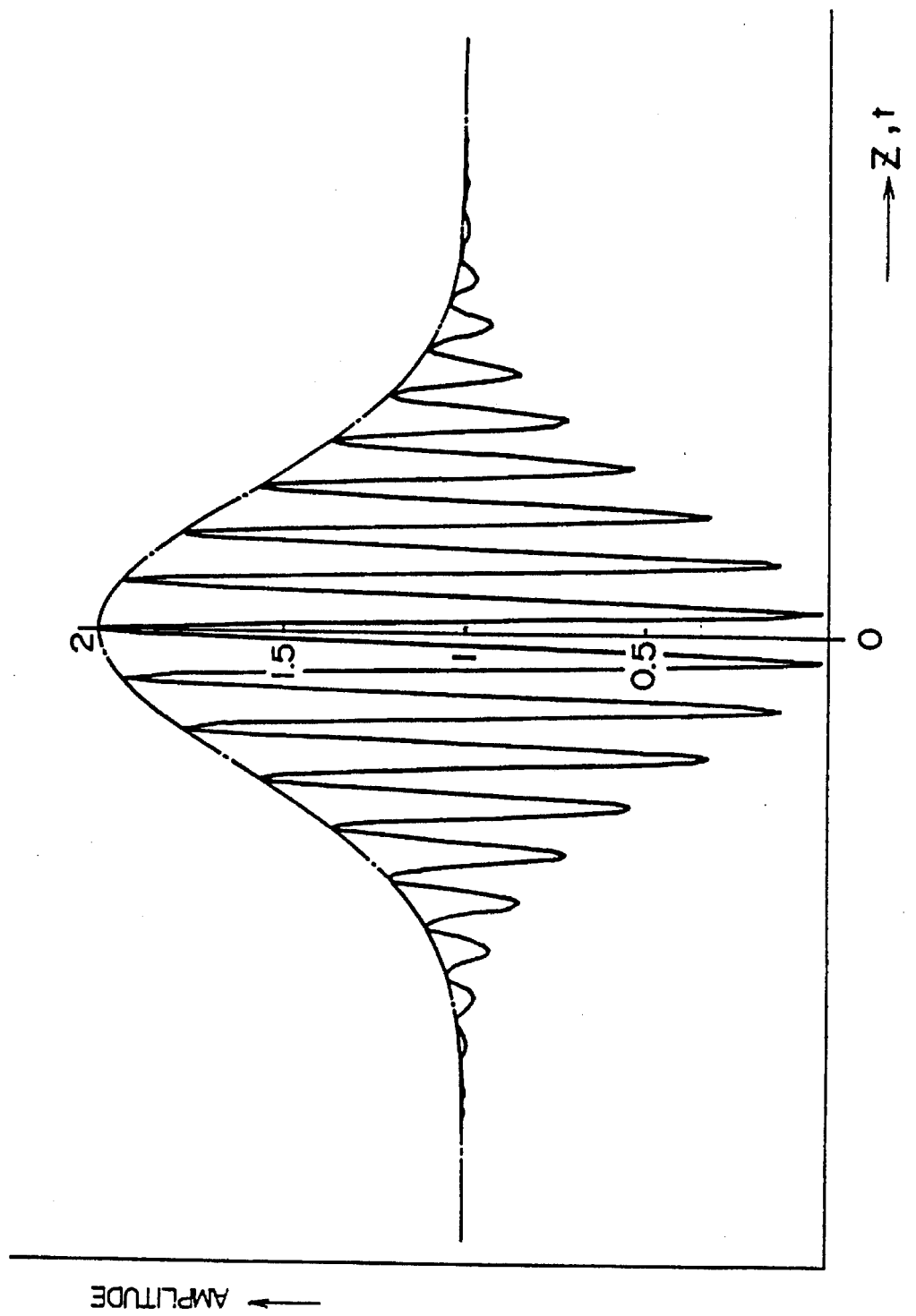
FIG. 27 is an illustration showing a light receiving signal in connection with the optical tomographic imaging equipment shown in FIG. 26.

Consequently, if the reflected light on only the point A is considered, the origin 0 in FIG. 27 appears at the point of the phase difference p=0. When the reference light generating unit 5 is moved, there appears between the top and bottom the phase difference corresponding to the half-wave of the wavelength of the center frequency of the light source (corresponding to ¼ wavelength in a movement amount of the reference light generating unit 5 because of the phase difference involved in the forward and backward runs of the light path). For example, in case of a1=a, there will be obtained a signal as shown in FIG. 27. The reason why the signal has a maximum value at p=0 and attenuates at both sides as shown in FIG. 27 is caused by a coherence length of the light source. In the state that scattering and reflecting members are distributed within the measuring object, there will be made up a synthetic signal of a group of signals which are obtained through shifting the signal shown in FIG. 27 with respect to time. Therefore, it is possible to implement a signal processing in the same fashion as that in an ultrasonic diagnostic system wherein an ultrasonic burst wave, which corresponds to the signal shown in FIG. 27, is projected on a biological sample, and reflected ultrasonic waves continuously scattered and reflected are received (refer to U.S. Pat. No. 4,140,022).

FIGS. 14, 15, 16A, 16B and 17 are explanatory views useful for understanding an electronic focusing control.

It is now considered that the function of light receiving is desired with an enhancement of only the reflected light from the point A (refer to FIGS. 2 and 3) within the measuring object. In order to avoid the troublesomeness, it is assumed that the point A is represented by a point $A_i$ which is a turning back point on a reflection plane of the beam splitter 3.

When reference light beams returning from a point B among the reference light beams are noticed, the majority of the reference light beams naturally pass through near the optical axis on the forward run. Hence, when a distribution of the difference in the optical path of the reference light beams to the beam locations is considered, it will be understood that the differences in the optical path are less on the forward run end, and a distribution of the differences in the optical path is determined with respect to the beam locations (for example, from a position of beam BH to a position of beam BI) on the backward run end (after reflection).

Figure 14:
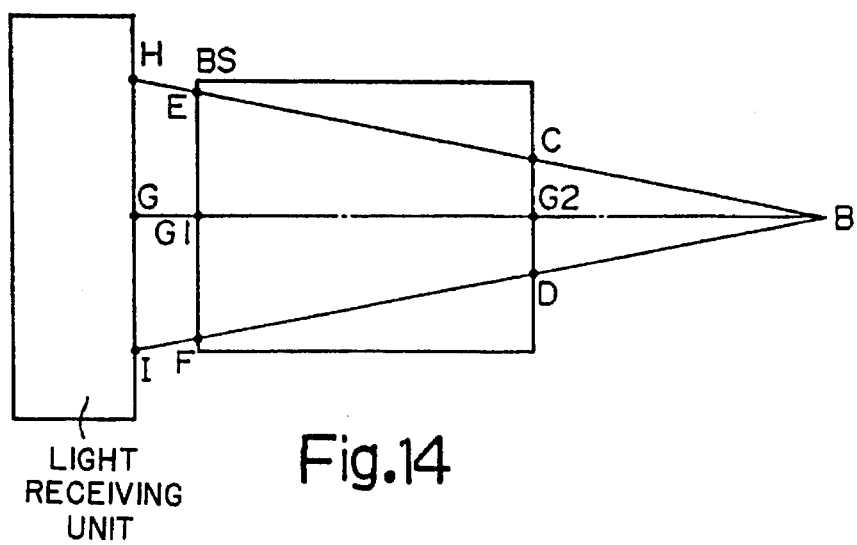
FIGS. 14, 15, 16A, 16B and 17 are explanatory views useful for understanding an electronic focusing control.

FIG. 14 is an illustration showing light paths on the backward run end of the reference light, which is applicable to both the directions in FIGS. 3 and 4. A leg of a perpendicular line extending from a point B toward the light-receiving plane of the light-receiving unit is represented by the alphabetical letter G. The intersections of the EF plane and the CD plane of the beam splitter BS with the leg BG are represented by G1 and G2, respectively. The alphabetical letters H and I define the light-receiving aperture with their edges. Generally, the portions G–G1 and G2–B are involved in the atmospheric circumferences, and are less than the beam splitter BS the refractive index. Consequently, while the points B, G2, G1 and G are on a straight line, the points B, C, E and H, and B, D, F and I are not on a straight line. However, since the refractive indexes of the respective portions and the relative position relations are determined, the light paths to the position of the point B may be beforehand determined through a calculation.

Figure 15:
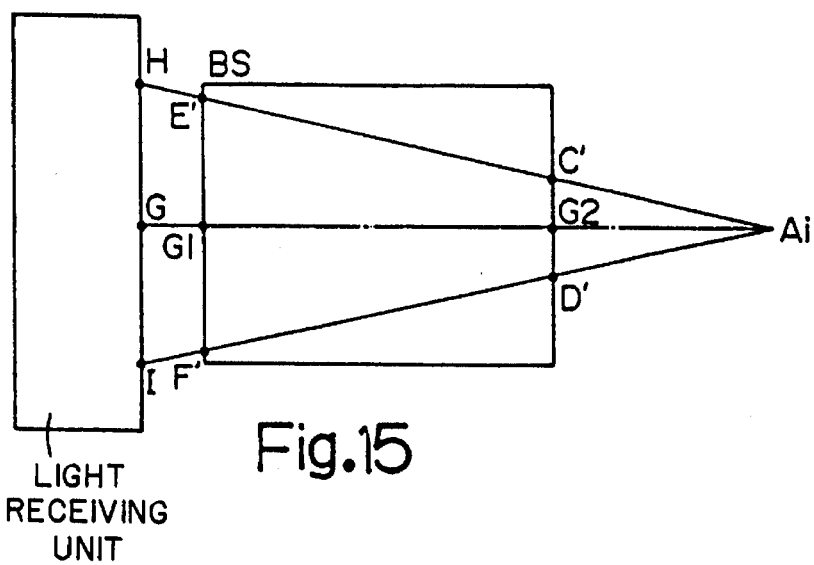

FIG. 15 is an illustration showing optical paths on the backward run end of the reflected light returned through the reflection on the point A (refer to FIGS. 3 and 4), which is applicable to both the directions in FIGS. 3 and 4. A point $A_i$ denotes a point of symmetric position of a point A (refer to FIGS. 3 and 4) with respect to a reflection plane (a HCGD plane in FIG. 2) of the beam splitter BS. A leg of a perpendicular line extending from the point $A_i$ toward the light-receiving plane of the light-receiving unit is represented by the alphabetical letter G. The intersections of the E'F' plane and the C'D' plane of the beam splitter BS with the leg $A_i$ G are represented by G1 and G2, respectively. The alphabetical letters H and I define the light-receiving aperture with its edges.

The reference light of BCD (FIG. 14) travels in the air. Generally, the measuring object is larger than air in refractive index (for example, 1.3–1.4 in the case of eyes). Hence, even if there is provided the same number of waves of light for the light beams entering the light path BG2 (FIG. 14) and the light path AiG2 (FIG. 15), the lengths of their light paths are not equal to each other, and are given by the relationship:

BG2 (FIG. 14)>$A_i$ G2 (FIG. 15)

To simplify the matter, if it is restricted to a case where a gap between a surface on the measuring object side of the beam splitter BS and the measuring object is sufficiently small, and in addition a surface of the measuring object may approximate a plane, the wavelength in the air / wavelength in the measuring object is equal to the refractive index of the measuring object / the refractive index of air. Therefore, if the following equation is satisfied, BG2 (FIG. 14) / $A_i$G2 (FIG. 15)

=a refractive index of the measuring object / a refractive index of air,
then the numbers of waves of light entering the light path BG2 (FIG. 14) and the light path $A_i$ G2 (FIG. 15) become equal to each other.

Figures 16A, 16B:
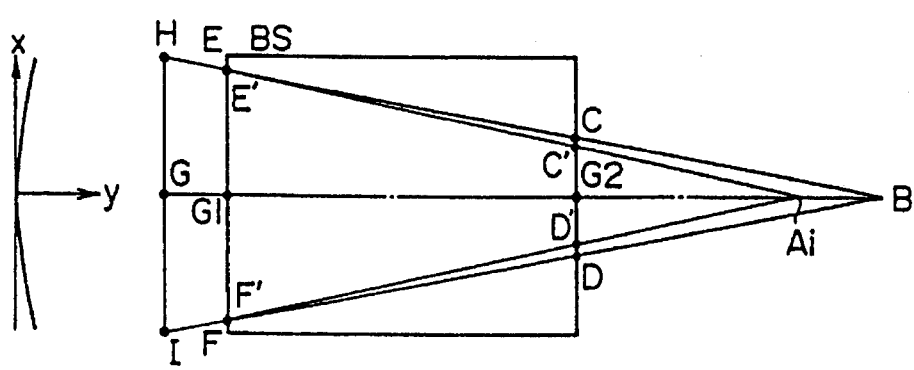

FIG. 16A shows an illustration in which both the light paths of the reference light and the reflected light are superposed on each other to satisfy the above mentioned condition.

Now, if a line parallel to the line BC through the point is drawn, and if the intersection of the created line and the plane CD is represented by C'' (not illustrated), there is provided the equation BC / $A_i$ C''=BG2 / $A_i$ G2. Thus, the same numbers of waves of light beams enter the light paths BC and $A_i$ C'', respectively. Whereas, in case of $A_i$ C'>$A_i$ C'', the number of waves of light entering the light path $A_i$ C' is more than that of the light path BC. In case of the point B being too far apart from the beam splitter BS, $A_i$ C'>$A_i$ C''.

In the determination of a distribution of the corresponding difference in the optical path between the plurality of the light paths within the light path limits BHI and the plurality of the light paths within the light path limits $A_i$ HI, there is provided a function as shown in FIG. 16B, where y denotes a difference in the number of waves; and x denotes an aperture position of the light-receiving element.

Thus, if output signals of the light-receiving element, which are derived through shifting by the delay amount corresponding to the number of waves difference (y) of each position of the light-receiving aperture, are selectively added in such a fashion that at the point H side of the aperture signals are received from the distance corresponding to the number of waves difference (y) farther than the point B (in case that the reference light generating unit goes away, a later signal in time), at the point G signals are received from the point B, and at the point I side of the aperture signals are received from the distance corresponding to the number of waves difference (y) farther than the point B (in case that the reference light generating unit goes away, a later signal in), focusing control is performed such that only the reflected light from the point A is emphasized.

Among the number of waves differences (y) on the respective positions of the light-receiving aperture, the parts involved in an integral multiple of the wave length λ of the light source do not undergo an aberration with respect to the carrier of the heterodyne signal. Accordingly, even if the electronic focusing control is conducted with respect to only the fraction parts less than the wave length λ of the light source, it is possible to attain a focusing effect to some degree (refer to d in FIG. 7).

Figure 17:
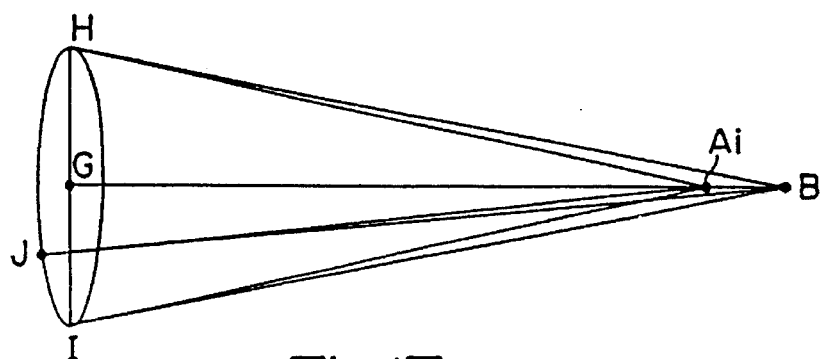

FIG. 17 is an illustration showing light paths regarding arbitrary directions without restriction of the scanning direction and the thickness direction, in which a leg of a perpendicular line extending from a point B toward the light-receiving plane of the light-receiving unit is denoted by the alphabetical letter G, and a point $A_i$ denotes a point of symmetric position of a point A (refer to FIGS. 3 and 4) with respect to a reflection plane (an HCGD plane in FIG. 2) of the beam splitter BS.

When an arbitrary point J is selected on the light-receiving plane of the light-receiving unit, the difference in the optical path may be determined by $A_i$ J G and BJG in the same fashion as in FIGS. 14, 15, 16A and 16B.

Figures 18A, 18B:
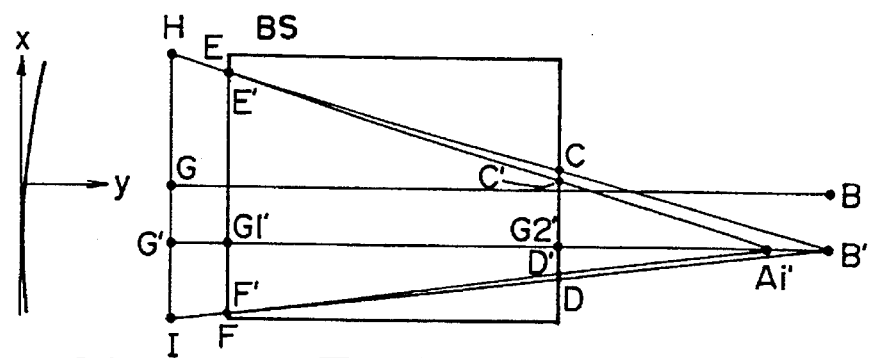
FIGS. 18A, 18B and 19A through 19D are explanatory views useful for understanding an electronic focusing control in a case where a plurality of pieces of received scanning lines is made up to a piece of object light beam through the electronic focusing control.

FIGS. 18A and 18B are explanatory views useful for understanding an electronic focusing control in a case where a plurality of pieces of a received scanning line are made up to a piece of an object light beam through the electronic focusing control. In this case, the reference light is provided with a spread (B—B').

It is now considered that a light reception is desired with an enhancement of only the reflected light from a point A' which is slightly deviated from the point A (refer to FIGS. 2 and 3) within the measuring object on an optical axis of an object light in the scanning direction or the thickness direction. The deviated point A' is concerned with an aberration less than output intervals of the light sources of the light source unit, or an aberration less than arrangement intervals of the light-receiving elements.

The point A', which is slightly deviated in the scanning direction, is taken when it is required that a plurality of receiving scanning lines is made up in the scanning direction. The point A', which is slightly deviated in the thickness direction, is taken when it is required that a plurality of receiving scanning lines is made up in the thickness direction with two dimensional array.

A leg of a perpendicular line extending from a point B toward the light-receiving plane of the light-receiving unit is represented by the alphabetical letter G. The alphabetical letters H and I define the light-receiving aperture with their edges. A point $A_i$ ' denotes a point of symmetric position of a point A' with respect to a reflection plane (a HCGD plane in FIG. 2) of the beam splitter BS. A leg of a perpendicular line fallen from the point $A_i$ ' toward the light-receiving plane of the light-receiving unit is represented by the alphabetical letter G'. The intersections of the E'F' plane and the C'D' plane of the beam splitter BS with the leg $A_i$ 'G' are represented by G1' and G2', respectively. On the straight line G' $A_i$ ', a point B' is given to satisfy B'G'=BG.

Generally, the portions G'–G1' and G2'–B' are involved in the atmospheric circumferences, and are less than the beam splitter BS in refractive index. Consequently, while the points B', G2', G1' and G' are on a straight line, the points B', C, E and H, and B', D, F and I are not on a straight line. However, since the refractive indexes of the respective portions and the relative position relations are determined, the light paths to the position of the point B' may be beforehand determined through a calculation.

The reference light of B'CD travels in air. Generally, the measuring object is larger than air in refractive index (for example, 1.3–1.4 in case of eyes). Hence, even if there is provided the same numbers of waves of light for the light beams entering the light path B'G2' and the light path $A_i$ 'G2', the lengths of their light paths are not equal to each other, and given by the relationships:

$$B'G2' > A_i 'G2',$$

To simplify the matter, if it is restricted to a case where a gap between a surface on the measuring object side of the beam splitter BS and measuring object is sufficiently small, and in addition a surface of the measuring object may approximate to the plane, the wavelength in the air / the wavelength in the measuring object is equal to a refractive index of the measuring object / a refractive index of the air. Therefore, if the following equation is satisfied, $$B'G2'/A_i'G2' = \text{a refractive index of the measuring object/a refractive index of air,}$$

then the numbers of waves of light entering the light path B'G2' and the light path $A_i$ 'G2' become equal to each other.

Now, if a line parallel to the line B'C through the point is drawn, and if the intersection of the created line and the plane CD is represented by C" (not illustrated), there is provided the equation B'C / $A_i$ 'C"=B'G2 / $A_i$ 'G2'. Thus, the same numbers of waves of light beams enter the light paths B'C and $A_i$ 'C", respectively. Whereas, in case of $A_i$ 'C'>$A_i$ 'C", the number of waves of light entering the light path $A_i$ 'C' is more than that of the light path B'C. In case of the point B being too far apart from the beam splitter BS, then $A_i$ C'>$A_i$ C".

In the determination of a distribution of the corresponding difference in the optical path between the plurality of light paths within the light path limits B'HI and the plurality of the light paths within the light path limits $A_i$ 'HI, there is provided a function as shown in FIG. 18B, where y denotes a difference in the number of waves; and x denotes an aperture position of the light-receiving element.

Thus, if output signals of the light-receiving element, which are derived through shifting by the delay amount corresponding to the number of waves difference (y) of each position of the light-receiving aperture, are selectively added in such a fashion that at the point H side of the aperture signals are received from the distance corresponding to the number of waves difference (y) farther than the point B' (in case that the reference light generating unit goes away, a later signal in time), at the point G' signals are received from the point B', and at the point I side of the aperture signals are received from the distance corresponding to the number of waves difference (y) farther than the point B' (in case that the reference light generating unit goes away, a later signal in time), there is provided a focusing control such that only the reflected light from the point A' is emphasized.

Among the number of waves differences (y) on the respective positions of the light-receiving aperture, the parts involved in an integral multiple of the wave length $\lambda$ of the light source do not undergo an aberration with respect to the carrier of the heterodyne signal. Accordingly, even if the focusing control (phase control) is conducted with respect to only the fraction parts less than the wave length $\lambda$ of the light source, it is possible to attain a focusing effect to some degree (refer to d in FIG. 7).

FIGS. 19A through 19D are explanatory views useful for understanding an electronic focusing control in a case where a plurality of pieces of a received scanning line are made up to a piece of an object light beam through the electronic focusing control. In this case, the reference light is provided with no spread.

It is now considered that a light reception is desired with an enhancement of only the reflected light from a point A' which is slightly deviated from the point A (refer to FIGS. 3 and 4) within the measuring object on an optical axis of an object light in the scanning direction or the thickness direction. The deviated point A' is concerned with an aberration less than output intervals of the light source of the light source unit, or an aberration less than arrangement intervals of the light-receiving element.

The point A', which is slightly deviated in the scanning direction, is taken when is required that a plurality of receiving scanning lines are made up in the scanning direction. The point A', which is slightly deviated in the thickness direction, is taken when it is required that a plurality of receiving scanning lines are made up in the thickness direction with a two dimensional array.

A leg of a perpendicular line extending from a point B toward the light-receiving plane of the light-receiving unit is represented by the alphabetical letter G. The intersections of the EF plane and the CD plane of the beam splitter BS with the leg BG are represented by G1 and G2, respectively. The alphabetical letters H and I define the light-receiving aperture with its edges. A point $A_i'$ denotes a point of symmetric position of a point A' with respect to a reflection plane (a HCGD plane in FIG. 2) of the beam splitter BS. A leg of a perpendicular line extending from the point $A_i'$ toward the light-receiving plane of the light-receiving unit is represented by the alphabetical letter G'. The intersections of the E'F' plane and the C'D' plane of the beam splitter BS with the leg $A_i'$G' are represented by G1' and G2', respectively.

Generally, the portions G–G1 and G2–B are involved in air, and are less than the beam splitter BS in refractive index. Consequently, while the points B, G2, G1 and G are on a straight line, the points B, C, E and H, and B, D, F and I are not on a straight line. However, since the refractive indexes of the respective portions and the relative position relations are determined, the light paths to the position of the point B may be beforehand determined through a calculation.

The reference light of BCD travels in the air. Generally, the measuring object is larger than air in refractive index (for example, 1.3–1.4 in case of eyes). Hence, even if there is provided the same numbers of waves of light for the light beams entered the light path BG2 and the light path $A_i'$G2', the lengths of their light paths are not equal to each other, and given by the relations:

$$BG2 > A_i'G2'.$$

To simplify the matter, if it is restricted to a case where a gap between a surface on the measuring object side of the beam splitter BS and the measuring object is sufficiently small, and in addition a surface of the measuring object may approximate a plane, the wavelength in air / the wavelength in the measuring object is equal to a refractive index of the measuring object / a refractive index of the air. Therefore, if the following equation is satisfied, $$BG2/A_i'G2' = \text{a refractive index of the measuring object/a refractive index of air,}$$

then the numbers of waves of light entered the light path BG2 and the light path $A_i'$G2' become equal to each other.

Figures 19A, 19B, 19C, 19D:
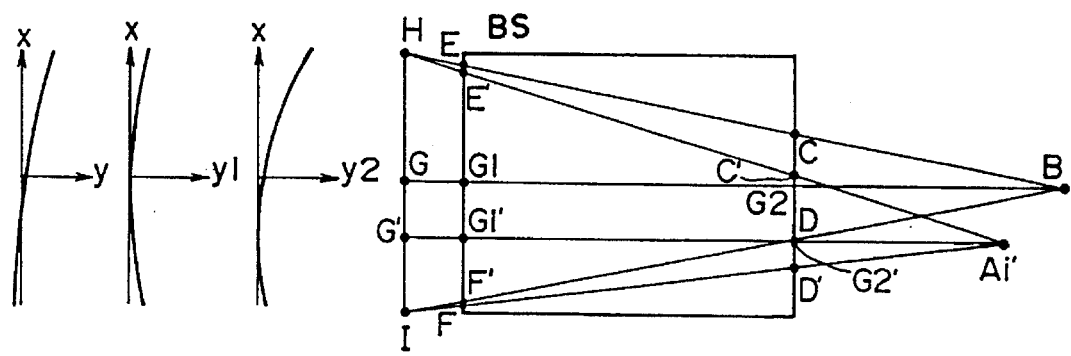

In the determination of a distribution of the differences in the optical path between the light path $A_i'$G' and the light paths within the light path limit $A_i'$HI, there is provided a function as shown in FIG. 19B, where y denotes a difference in the number of waves; and x denotes an aperture position of the light-receiving element.

In the determination of a distribution of the differences in the optical path between the light path BG and the light paths within the light path limits BHI, there is provided a function as shown in FIG. 19C, where y denotes a difference in the number of waves; and x denotes an aperture position of the light-receiving element.

In the determination of a distribution of the differences in the optical path between the light paths within the light path limits BHI and $A_i'$HI, there is provided a function as shown in FIG. 19D, where y denotes a difference in the number of waves; and x denotes an aperture position of the light-receiving element.

Thus, if output signals of the light-receiving element, which are derived through shifting by the delay amount corresponding to the number of waves difference (y) of each position of the light-receiving aperture, are selectively added in such a fashion that at the point H side of the aperture signals are received from the distance corresponding to the number of waves difference (y) farther than the point B (in case that the reference light generating unit goes away, a later signal in time), at the point G signals are received from the distance corresponding to the number of waves difference (y) farther than the point B (in case that the reference light generating unit goes away, a later signal in time), and at the point I side of the aperture signals are received from the distance corresponding to the number of waves difference (y) nearer than the point B' (in case that the reference light generating unit goes away, a former signal in time), there is provided focusing control such that only the reflected light from the point A' is emphasized.

As stated above, among the number of waves differences (y) on the respective positions of the light-receiving aperture, the parts involved in an integral multiple of the wave length $\lambda$ of the light source do not undergo an aberration with respect to the carrier of the heterodyne signal. Accordingly, even if the focusing control (phase control) is conducted with respect to only the fraction parts less than the wave length $\lambda$ of the light source, it is possible to attain a focusing effect to some degree.

In this manner, it is possible to focus on the point A, and also to focus on a plurality of points neighboring on the point A. Further, it is possible to provide a plurality of scanning lines to a piece of object light beam by means of sequentially changing a pattern of the delay.

In a case where the gap between a surface of the beam splitter BS at the measuring object side and the measuring object can not be ignored, there may be provided such an arrangement that the gap between the surface of the beam splitter BS at the measuring object side and the measuring object is adjustable so that the surface of the beam splitter BS at the measuring object side is located at a predetermined position.

Further, in a case where a surface of the measuring object can not approximate a plane, it is acceptable to use a delay pattern approximating a predetermined configuration according to a measuring object, or also acceptable to estimate a configuration of a surface of the measuring object from a time-waveform of a light-receiving signal. It is acceptable that the refractive index of the measuring object is detected beforehand in the form of clinical data. Further, in a case where the measuring object is of a multilayered structure having different refractive indexes, it is acceptable that boundaries of the layers are detected from a time-waveform of a light-receiving signal, and a light path at the measuring object side is calculated using a map of clinical data related to the refractive indexes of the respective layers.

Figure 20:
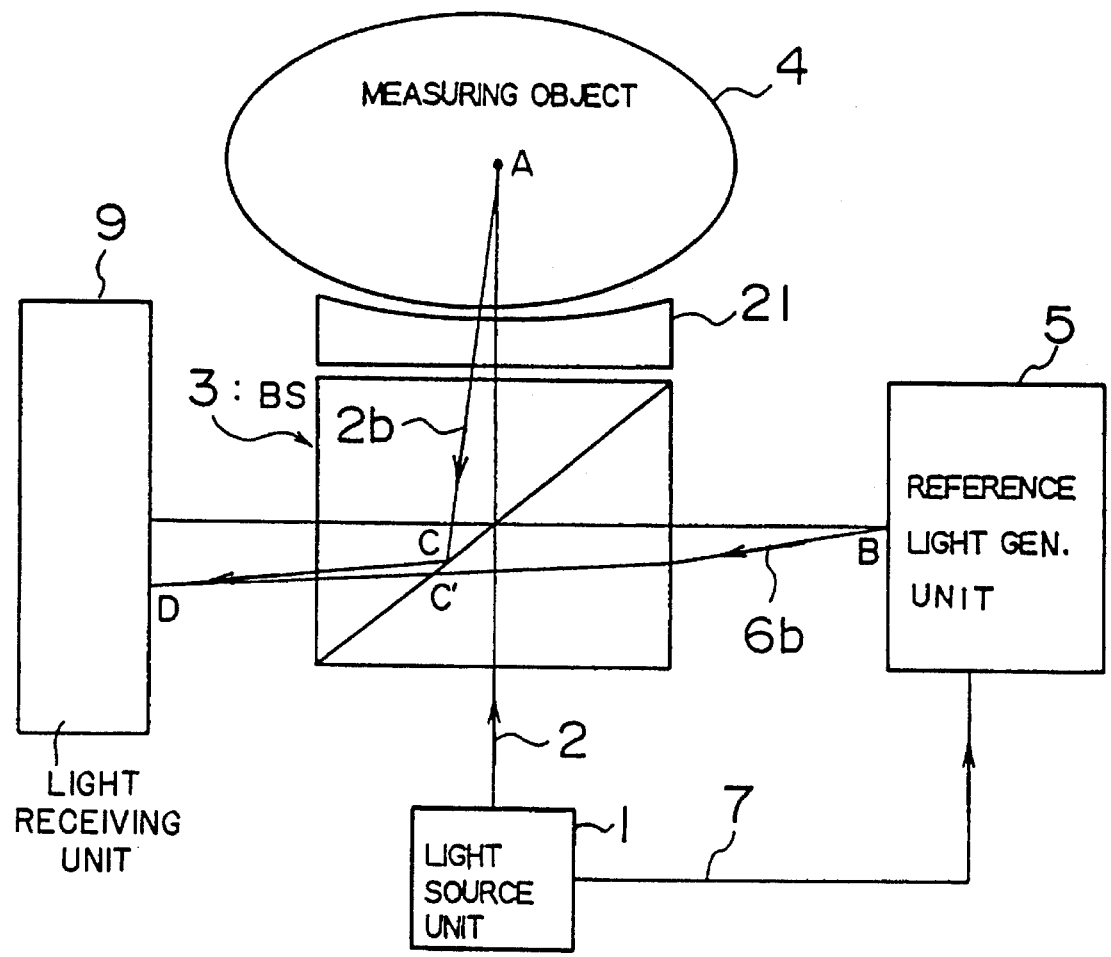
FIG. 20 is an illustration showing an example in which a correcting plate is inserted to regulate a light path.

FIG. 20 is an illustration showing an example in which a correcting plate consisting of glass or the like having a suitable refractive index, which is of a suitable shape with respect to the scanning direction and the thickness direction, according to the measuring object, is inserted between a surface of the beam splitter BS at the measuring object side and a surface of the measuring object to regulate a light path.

A light path is branched into two ways one being a light path along which light emitted from a light source mounted on a light source unit 1 travels toward a reference light generating unit 5 and another being a light path along which the light emitted from the light source mounted on the light source unit 1 travels toward a beam splitter (BS) 3. Assuming that points within a reflection plane of the beam splitter 3 are given by C and C' as shown in the figure; it is supposed that reference light is emitted from the reference light generating unit 5 via a light path 6b through the point C' to a point D; and it is supposed that reflected light passing through the beam splitter 3 and reflected on a point A of a measuring object 4 passes via a light path 2b through the point C to the point D, and the light-receiving unit 9 may detect a heterodyne signal having phase information corresponding to the phase difference between the reference light and the reflected light. Hence, it is possible to regulate the light path by means of insertion of a correcting plate 21 having a suitable refractive index, which is of a suitable shape with respect to the scanning direction and the thickness direction, according to the measuring object 4. Further, the correcting plate 21 is effective to observe the neighborhood of a surface of the measuring object 4.

Figure 21:
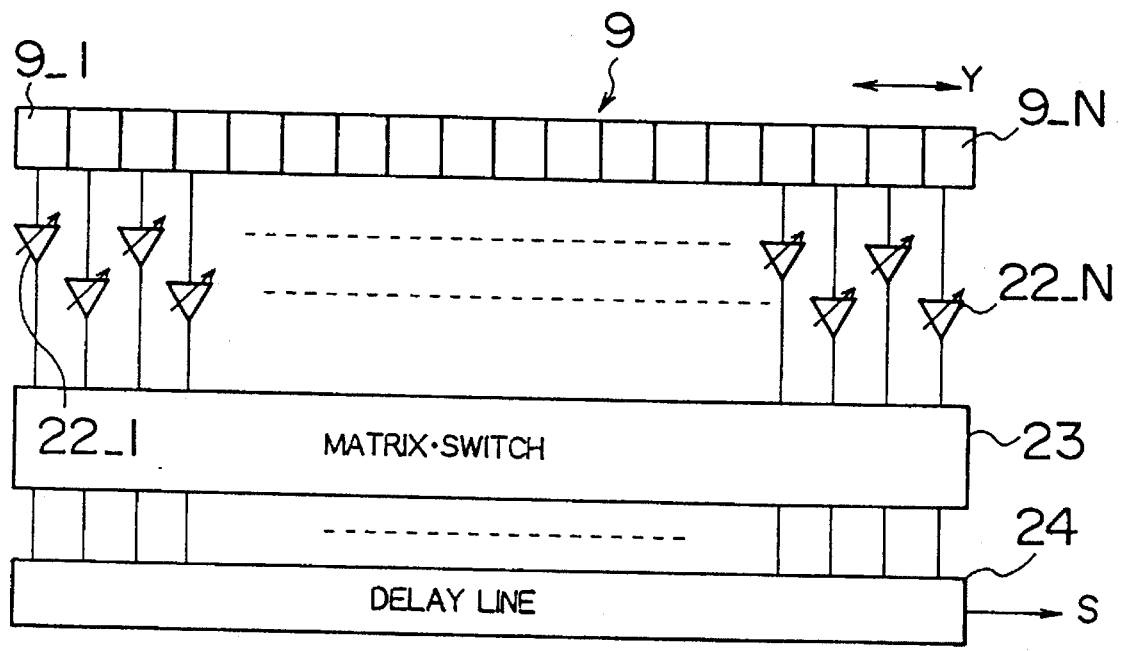
FIG. 21 is a block diagram showing a basic arrangement of constituents of a light-receiving unit and an electronic focusing control unit in the optical tomographic imaging equipment according to the embodiment shown in FIG. 1.

FIG. 21 is a block diagram showing a basic arrangement of constituents of a light-receiving unit and an electronic focusing control unit in the optical tomographic imaging equipment according to the embodiment shown in FIG. 1.

A light-receiving unit 9 comprises a plurality of photo-electric elements $9\_1, \ldots, 9\_N$, which are arranged in the Y-direction, a plurality of amplifiers $22\_1, \ldots, 22\_N$, each coupled to the associated photo-electric element to amplify the photo-electric signal from the photo-electric element, a matrix switch 23 coupled to the plurality of amplifiers $22\_1, \ldots, 22\_N$, and an analog delay line 24 coupled to the matrix switch 23.

Each of the amplifiers $22\_1, \ldots, 22\_N$ is a variable gain amplifier. It is possible to define the light-receiving aperture on a variable basis through control of the gain of each of the amplifiers $22\_1, \ldots, 22\_N$, and if the larger gain of the amplifier is set up for a signal which is derived from the photo-electric element at the center of the light-receiving aperture, and the smaller gain of the amplifiers are set up for signals which are derived from the photo-electric elements nearer the edges of the light-receiving aperture, it is possible to obtain a constant beam width of scanning line independently of a the depth within the subject, that is, to implement a so-called apodization.

Outputs of the matrix switch 23 are each connected to the associated tap of the analog delay line 24. Thus, in the matrix switch 23, the photo-electric signals derived from the photo-electric elements $9\_1, \ldots, 9\_N$ are switchingly coupled to the taps of delay line 24 on an adaptive basis. Consequently, the delay line 24 outputs signals which are produced in such a manner that the photo-electric signals derived from the photo-electric elements are adaptively delayed and added each other.

Figure 22:
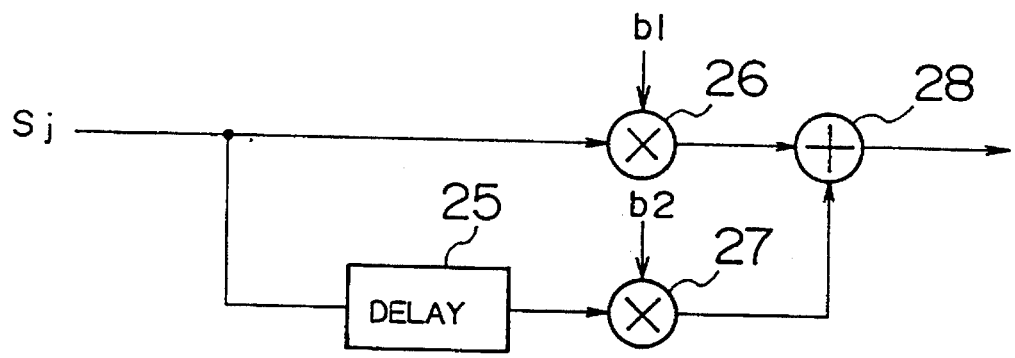
FIG. 22 is a block diagram showing a part corresponding to a photo-electric element in another basic arrangement of constituents of an electronic focusing control unit in the optical tomographic imaging equipment according to the embodiment shown in FIG. 1.

FIG. 22 is a block diagram showing a part corresponding to a photo-electric element in another basic arrangement of constituents of an electronic focusing control unit in the optical tomographic imaging equipment according to the embodiment shown in FIG. 1.

The photo-electric signal $S_j$, which is derived from the j-th photo-electric element is branched into two ways toward a delay circuit 25 and a multiplier 26. In the delay circuit 25, the input signal $S_j$ is delayed by a predetermined time $\tau$ and outputted therefrom. The output signal from the delay circuit 25 is passed to a multiplier 27. In the multipliers 26 and 27, the input signals are multiplied by the associated coefficients, respectively, and then passed to an adder 28, and added to each other.

Next, it will be explained that the arrangement shown in FIG. 22 permits a signal delay (phase) to be variably controlled.

When an output of the j-th photo-electric element at time t is expressed by $$I_j(t) = a(t) \cos(p + \epsilon t),$$

an output at time t−τ is expressed by $$I_j(t-\tau) = a(t-\tau) \cos(p + \epsilon(t-\tau)).$$

If the time τ takes a sufficiently small value, the following equation may be given $$a(t) \doteq a(t-\tau).$$

Now, the following equation is defined $$I_{j\,d} = a(t) [b1 \cdot \cos(p + \epsilon t) + b2 \cdot \cos(p + \epsilon(t-\tau))].$$

If b1 and b2 are defined as follows:

$$b1 = \sin(-\Phi + \epsilon\tau) / \sin(\epsilon\tau)$$

$$b2 = \sin(\Phi) / \sin(\epsilon\tau)$$

the above noted $I_{j\,d}$ may be expressed as follows;

$$I_{j\,d} = a(t) \cdot \cos(p + \epsilon t - \Phi),$$

Thus, it is possible to perform a phase control so as to provide an optional phase Φ. When $\epsilon\tau = \pi/2$, then $b1 = \cos(\Phi)$ and $b2 = \sin(\Phi)$. Thus, it is possible to optionally select Φ between 0–2π.

When $\epsilon\tau = \pi/2$, the delay time τ is expressed by $\tau = \lambda/8/v$ where λ denotes a wavelength of light. Thus, in accordance with the circuit arrangement as shown in FIG. 22, an output signal of the photo-electric signal is branched into two ways, toward the delay circuit 25 and the multiplier 26. In the delay circuit 25, the input signal is delayed by the time τ and outputted therefrom. The output signal from the delay circuit 25 is passed to the multiplier 27. In the multipliers 26 and 27, the input signals are multiplied by the associated coefficients b1 and b2, respectively, and then passed to the adder 28 to be added. In this manner, it is possible to obtain a resultant signal $I_{j\,d}$ which has been subjected to the desirable phase control. Further, it is possible to make up the resultant signal $I_{j\,d}$ subjected to the phase control in such a manner that an A/D converter is used to implement a sampling in suitable sampling times. Two pieces of data, which are obtained through the sampling and mutually different in sampling time, are selected to be multiplied by the associated suitable coefficients and then added. Incidentally, in FIG. 22, it is acceptable to reverse the delay circuit 25 and the multiplier 27 in the arrangement order.

Figure 23:
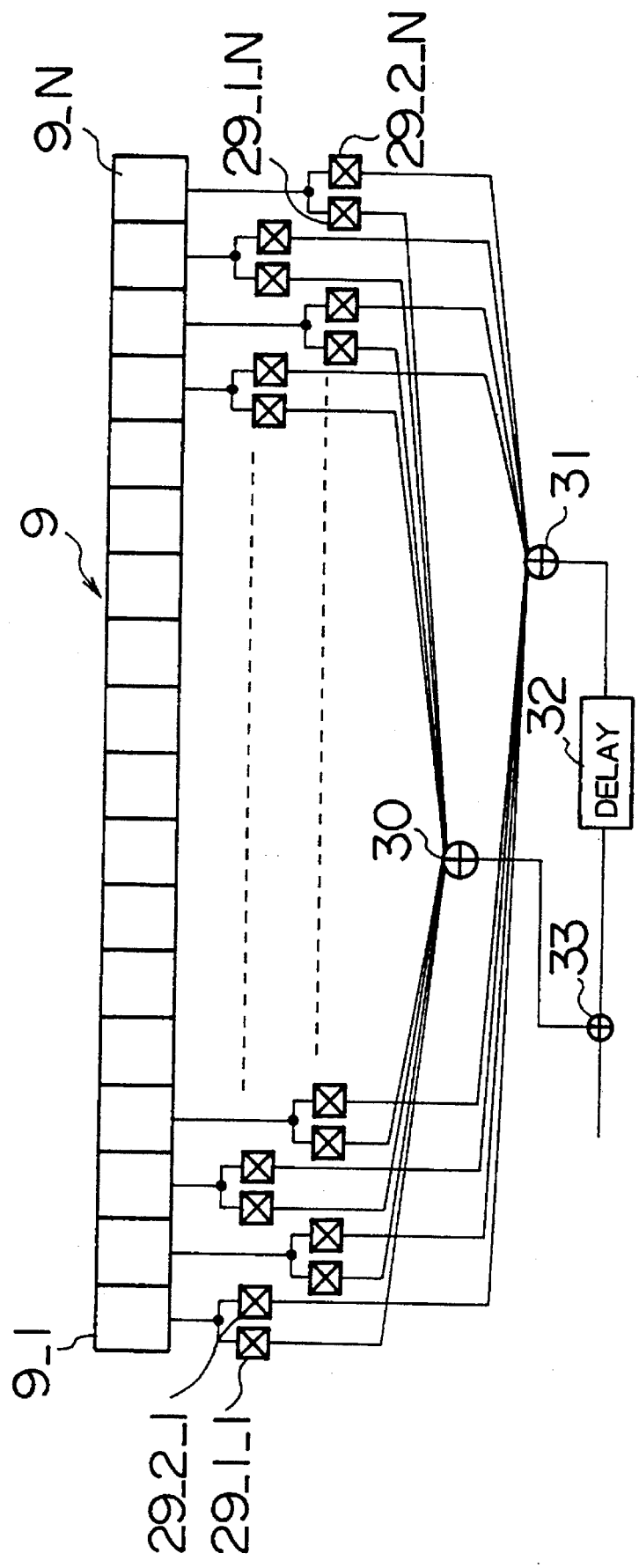
FIG. 23 is a block diagram showing still another basic arrangement of constituents of an electronic focusing control unit in the optical tomographic imaging equipment according to the embodiment shown in FIG. 1.

FIG. 23 is a block diagram showing still another basic arrangement of constituents of an electronic focusing control unit in the optical tomographic imaging equipment according to the embodiment shown in FIG. 1. According to this example, a single delay line is used to implement the above-described phase control.

A light-receiving unit 9 comprises a plurality of photo-electric elements $9\_1, \ldots, 9\_N$ coupled through buffer amplifiers (not illustrated) to the associated pair multipliers $29\_1\_1, 29\_2\_1; \ldots, 29\_1\,N, 29\_2\_N$, each of which is provided with an independent coefficient, respectively. Outputs of the multipliers $29\_1\_1, \ldots, 29\_1\_N$, which are connected to the photo-electric elements $9\_1, \ldots, 9\_N$, respectively, are added in an adder 30 and then inputted to an adder 33. Whereas outputs of the multipliers 29_2_1, . . . , 29_2_N are added an adder 31 and then inputted through a delay circuit 32 to the adder 33. The above-described two inputs are added to each other in the adder 33. If an A/D converter and a memory are connected to an output of the adder 33, it will be possible to calculate several received scanning lines for a transmission and store the results in the memory. For example, if an interval of irradiation (transmission) of the object light is given by 100 μm, it is possible to generate ten received scanning lines with a 10 μm interval. It is sufficient in this scheme to provide a single delay circuit, thereby being economical. On the other hand, according to this scheme, since the delay circuit is disposed after the multiplier, it is obliged, when the coefficient is changed, to wait a stabilized state from the transient state. Thus, it is impossible to expect a high speed operation. For a high speed operation, as shown in FIG. 22, it is necessary to provide the delay circuit on each photo-electric element and, in addition, to provide the multiplier at an output of the delay circuit.

According to the circuit system using such a multiplier (variable gain amplifier), it is possible to select the light-receiving aperture by means of setting the coefficient (control data) to zero, and it is possible to automatically perform the control of the light-receiving aperture and the scan of the scanning line only through shifting the coefficient (control data) of the multiplier in accordance with the change of the scanning lines.

Figure 24:
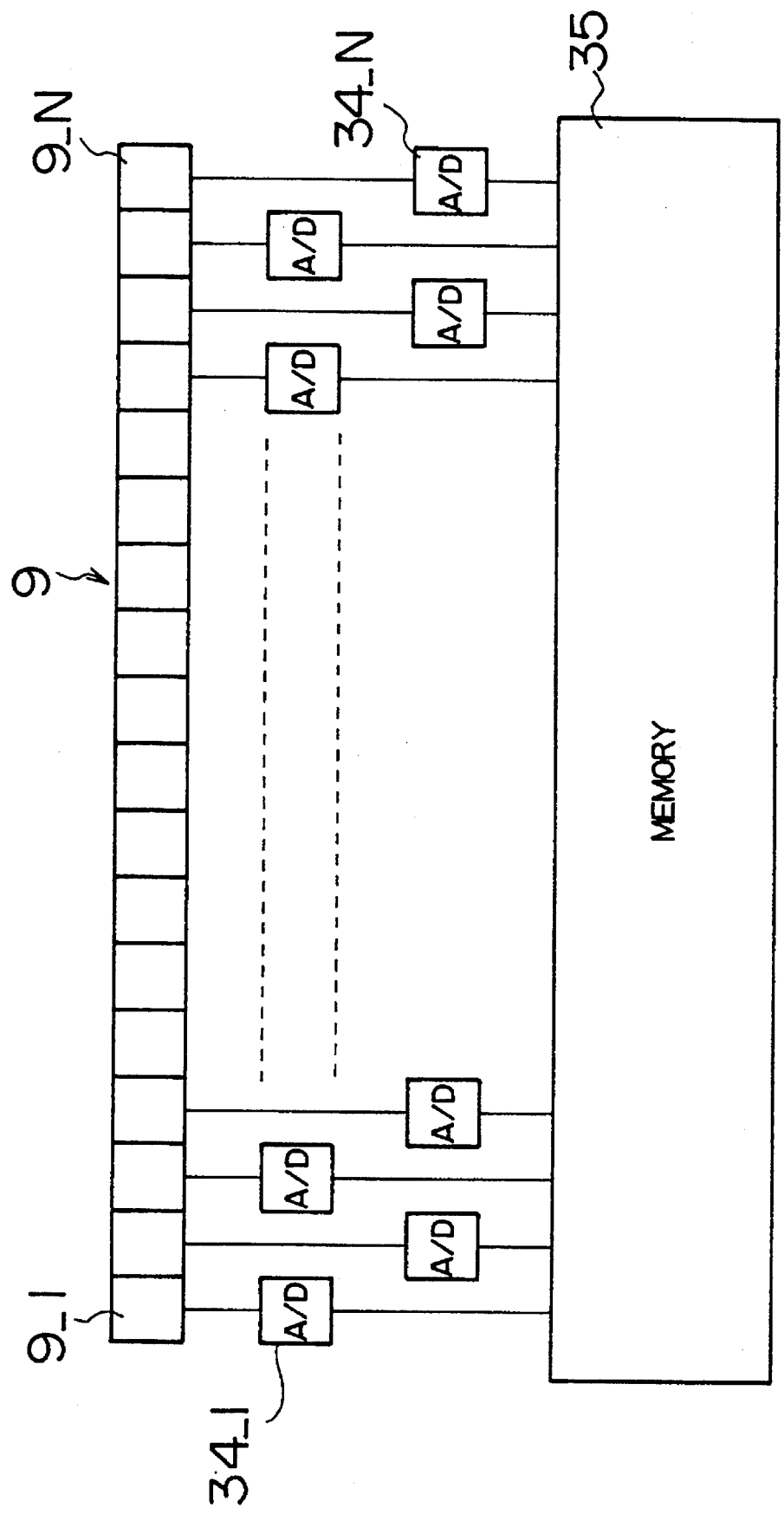
FIG. 24 is a block diagram showing still another basic arrangement of constituents of an electronic focusing control unit in the optical tomographic imaging equipment according to the embodiment shown in FIG. 1.

FIG. 24 is a block diagram showing still another basic arrangement of constituents of an electronic focusing control unit in the optical tomographic imaging equipment according to the embodiment shown in FIG. 1. In this example, an A/D converter is used as delay means for the photo-electric signal.

A light-receiving unit 9 comprises a plurality of photo-electric elements 9_1, . . . , 9_N coupled through buffer amplifiers (not illustrated) to the associated A/D converters 34_1, . . . , 34_N, respectively. Outputs of the A/D converters 34_1, . . . , 34_N are connected to a memory 35.

If the sampling time $\tau1=\lambda/8/v$, then $\epsilon\tau=\pi/2$. Thus, it is possible to take in a signal which has a phase shift by 90 degrees with respect to a Doppler frequency, and thus to perform the same phase control as mentioned above. Further, if the signals having the interval $\tau2=\lambda/2/v$ are sampled, signals, which are subjected to a delay of an integral multiple of the wave, are also available. Therefore, it is also possible to perform a focusing control on the basis of the combination of the delay of an integral multiple of the wave and the phase control (a control for a delay less than wavelength).

Further, it will be possible to implement an apodization of the light-receiving aperture, and to make up a plurality of scanning lines for a transmission, through calculation based on the signals stored in the memory.

Figure 25:
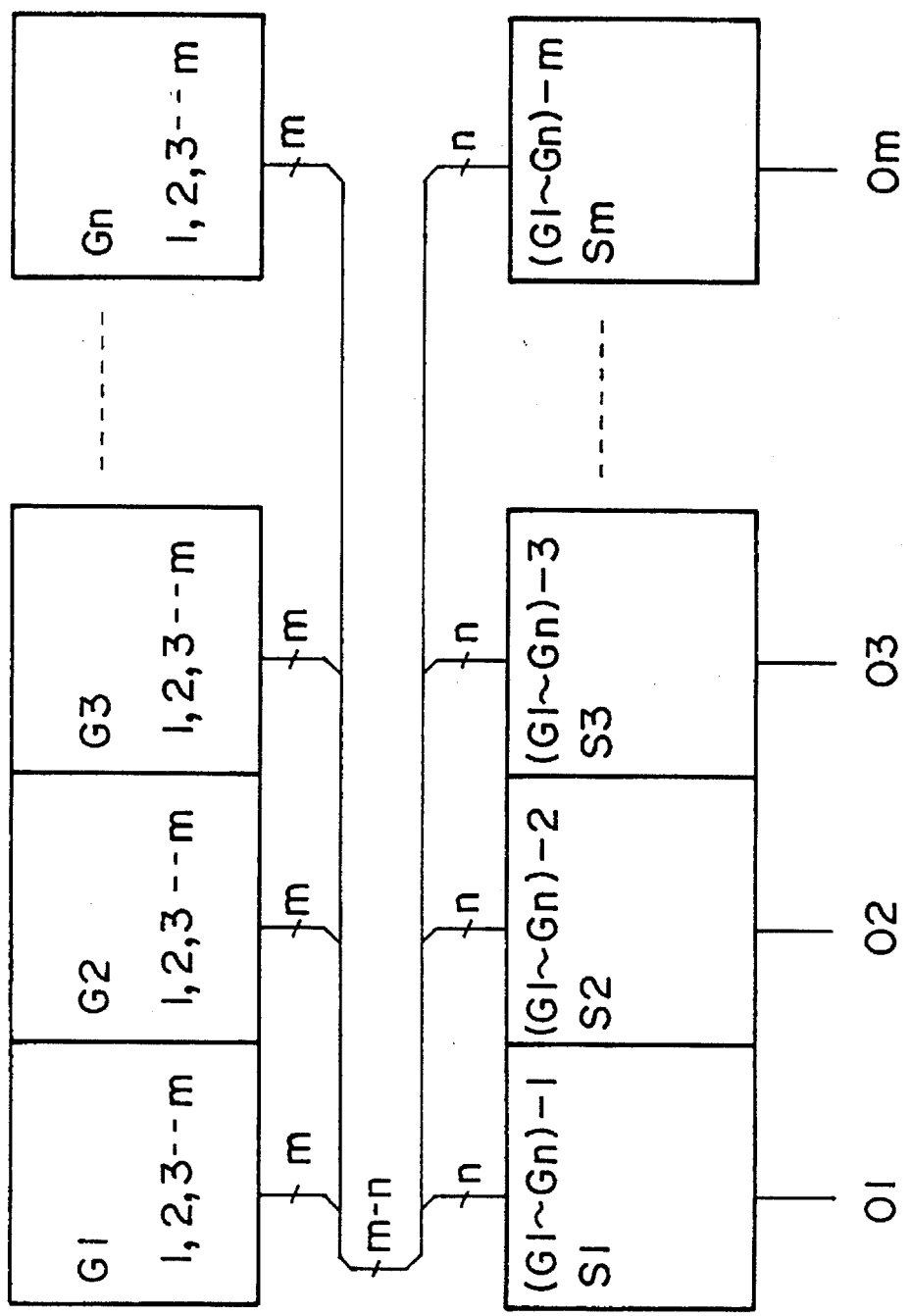
FIG. 25 is a block diagram showing another basic arrangement of constituents of a light-receiving unit.

FIG. 25 is a block diagram showing another basic arrangement of constituents of a light-receiving unit. In this example, the light-receiving unit comprises a CCD having parallel outputs, and a read function of the CCD is utilized for the scan of the light-receiving aperture.

In a case where the light-receiving aperture is constituted of m pieces of element, photo-electric elements of the CCD are placed in a group in units of m pieces of element. In this example, they are made up groups G1–Gn. It is noted that even if the group Gn is constituted of a number of the elements less than m, the following explanation is applicable.

The respective first elements of the groups G1–Gn are connected to n pieces of an input terminal of a read function unit S1 of the CCD, respectively. In the read function unit S1, one input of those is selected and outputted to an output terminal 01.

This is the similar also with respect to other read function units S2, . . . , Sm. For example, regarding the read function unit Sm, only the respective m-th elements of the groups G1–Gn are connected to n pieces of input terminal of a read function unit Sm of the CCD, respectively. In the read function unit Sm, one input of those is selected and outputted to an output terminal Om.

Using the CCD in which the groups of the photo-electric elements and the read function units are connected as described above, if there is provided a connection such that the signals inputted from the group G1 are outputted to the output terminals O1–Om of the read function units S1–Sm, respectively, m pieces of element of group G1 may be selected.

Next, if the signals of the group G2 are selected with respect to only the read function unit S1, it is equivalent that the light-receiving aperture is scanned by the corresponding one element in the right direction of FIG. 25.

Further, if the signals of the group G2 are selected with respect to the read function unit S2, it is equivalent that the light-receiving aperture is scanned by the corresponding two elements in the right direction.

In the similar fashion, it is possible to optionally perform the scan in units of elements for the light-receiving aperture.

If there are provided a plurality of arrangements as mentioned above, it is possible also to deal with also a two-dimensional array in a similar fashion.

According to the example, it is possible to maintain a higher speed through the parallel output, and in addition, to reduce the number of output pins through utilization of the read function of the CCD in the scanning direction.

Figure 26:
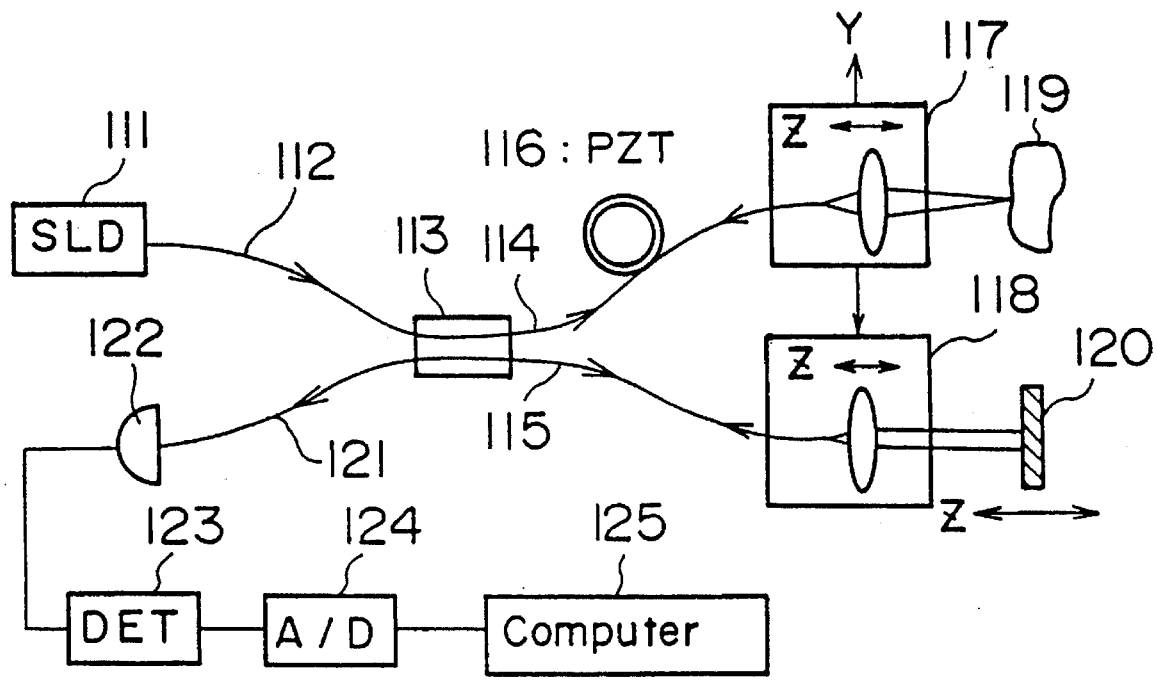
FIG. 26 shows an explanatory view useful for understanding the conventional optical tomographic imaging equipment.

While the present invention has been described referring to the embodiments using the beam splitter 3 shown in FIG. 1 and the modification, the present invention is not restricted to the arrangement using the beam splitter 3. It is acceptable to arrange the system in such a manner that a plurality of fiber-couplers, for example, as shown in FIG. 26, are used so that the light source is associated with only the specified fiber-coupler to split the light into the object light and the reference light, and the object light and the reference light are introduced to the light-receiving unit with their superposition. Further, according to the embodiments as described above, the scan is conducted through switching over a plurality of light sources. However, there is no need to provide a plurality of light sources. It is acceptable to conduct the scan by means of, for example, moving the emission end of the optical fiber in the scanning direction, or moving the light source.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

We claim:

1. An optical tomographic imaging equipment comprising:

a light source unit, having a light source for radiating a light wave having a predetermined coherence length, for splitting the light wave radiated from said light source into a first light wave and a second light wave and emitting the same;

a light-receiving unit having a plurality of light-receiving elements;

an object unit for introducing the first light wave emitted from said light source unit into a subject in a form of an object light irradiating the subject, and introducing into said light-receiving unit a reflected light obtained through reflection of the object light from the subject;

a reference light generating unit for converting the second light wave received from said light source unit into a reference light having a frequency shifted from that of the second light wave by continuously varying an optical path as a travelling path of the second light wave to said light-receiving unit, and introducing the reference light to said light-receiving unit wherein at least part of the reference light is superposed on the reflected light in said light-receiving unit;

said light-receiving elements generating a corresponding plurality of light-receiving signals in response to reception of an interference wave resulting from superposition of the reflected light and the reference light; and an electronic focusing control unit for relatively delaying and adding said plurality of light-receiving signals to one another to generate a resultant light-receiving signal involved in emphasis of information of a predetermined point on a light path of the object light within the subject.

2. An equipment according to claim 1, wherein said light source unit comprises scanning means for sequentially varying an emission position of the first light wave so that a scan of the subject by the object light can be performed.

3. An equipment according to claim 2, wherein said light source unit has a plurality of light sources for supplying a corresponding plurality of the object lights different from each other in light paths, and the scan of the subject by the object lights is performed by sequentially turning on said plurality of light sources.

4. An equipment according to claim 1, wherein said light source unit comprises an optical fiber for transmitting the light wave emitted from said light source.

5. An equipment according to claim 4, wherein said light source unit has a fiber-coupler for splitting the light wave transmitted via said optical fiber into the first light wave and the second light wave, said fiber-coupler being disposed in mid course of said optical fiber.

6. An equipment according to claim 5, wherein optical fiber portions, through which the first light wave and the second light wave are transmitted, respectively, have a same length of optical paths as each other.

7. An equipment according to claim 1, wherein said light source unit comprises:

a collimating optical system in which the second light wave is emitted in a form of a collimated beam toward said reference light generating unit; and wherein said reference light generating unit comprises an optical fiber having first and second ends, said optical fiber emitting the reference light from the first end in the form of beam spreading in a cone shape, and an incident optical system in which the second light wave in the form of the collimated beam is converged and enters through the second end of said optical fiber.

8. An equipment according to claim 1, wherein said reference light generating unit comprises a scattering optical system having an average surface roughness which is finer than a center wavelength of the light wave.

9. An equipment according to claim 2, wherein each of said plurality of light-receiving elements of said light-receiving unit is arranged in a scanning direction in which the reflected light travels in said light-receiving unit in response to a scan of the subject by the object light.

10. An equipment according to claim 9, wherein said reference light generating unit is movable in accordance with an operation of varying an optical path of the reference light, and comprises a cylindrical optical system for correcting the optical path of the reference light introduced into said light-receiving unit with respect to a thickness direction intersecting the scanning direction.

11. An equipment according to claim 2, wherein:

said plurality of light-receiving elements of said light-receiving unit is arranged on a two-dimensional basis, in a scanning direction in which the reflected light travels in said light-receiving unit in response to a scan of the subject by the object light, and in a thickness direction intersecting the scanning direction; and said electronic focusing control unit relatively delays and adds said plurality of light-receiving signals to one another with respect to both the scanning direction and the thickness direction.

12. An equipment according to claim 1, wherein said electronic focusing control unit relatively delays and adds said plurality of light-receiving signals to one another while sequentially varying a relative delay pattern so as to issue a resultant light-receiving signal involved in emphasis of information of a plurality of predetermined points aligned on a scanning line extending to a light path of the object light irradiated on the subject.

13. An equipment according to claim 1, wherein said electronic focusing control unit relatively delays and adds said plurality of light-receiving signals to one another while sequentially varying a relative delay pattern so as to issue a resultant light-receiving signal involved in emphasis of information of a plurality of predetermined points aligned on each of a plurality of scanning lines extending to a light path of the object light.

14. An equipment according to claim 3, wherein said electronic focusing control unit, with respect to each of a plurality of said object lights according to the light waves emitted from said plurality of light sources, relatively delays and adds said plurality of light-receiving signals to one another while sequentially varying a relative delay pattern so as to issue a resultant light-receiving signal involved in emphasis of information of a plurality of predetermined points aligned on each of a plurality of scanning lines extending to a light path of the object light.

15. An equipment according to claim 1, wherein said light source unit simultaneously emits a plurality of said object lights which are different from each other in their light paths, and said electronic focusing control unit relatively delays and adds said plurality of light-receiving signals to one another while sequentially varying a relative delay pattern so as to issue a resultant light-receiving signal involved in emphasis of information of a plurality of predetermined points aligned on respective ones of a plurality of scanning lines respectively extending to the plurality of the light paths of object lights, and at least one scanning line extending to each light path of each object light.

16. An equipment according to claim 1, wherein said electronic focusing control unit has a plurality of delay lines each delaying on a variable delay amount basis an associated one of the light-receiving signals derived from said plurality of light-receiving elements.

17. An equipment according to claim 1, wherein said electronic focusing control unit comprises delay means for delaying the light-receiving signals on a variable delay amount basis by a weighting addition on a variable weighted amount basis, wherein said electronic focusing control unit divides each of the light-receiving signals derived from said plurality of light-receiving elements into a pair of divided signals to produce an associated one signal and an associated other signal, and delays one of the pair of divided signals by a predetermined delay amount with respect to that of the other one of the pair of divided signals, and operates an associated weighting operation on a variable weighted amount basis to produce the associated one signal, and operates an associated weighting operation on a variable weighted amount basis to produce the associated other signal, and adds the associated one signal and the associated other signal to each other to produce an associated addition signal.

18. An equipment according to claim 1, wherein said electronic focusing control unit comprises:

pairs of weighted adder means as a part of delay and addition means, wherein first ones of said pairs of weighted adder means perform a weighing addition on a variable weighted amount basis for each of the light-receiving signals to produce associated one addition signals and second ones of said pairs of weighted adder means perform a weighing addition on a variable weighted amount basis for each of the light-receiving signals to produce associated other addition signals; and said delay and addition means for delaying the associated one addition signals by a predetermined delay amount with respect to that of the associated other addition signals and adding the delayed associated one addition signals with the associated other addition signals to produce associated addition signals which are equivalent to said resultant light-receiving signal.

19. An equipment according to claim 1, wherein one of said light-receiving unit and said electronic focusing control unit has an aperture definition means for optionally defining a light-receiving aperture comprising said light-receiving elements for obtaining the light-receiving signals to be added to each other by said electronic focusing control unit, said aperture definition means comprising at least part of plural light-receiving elements among the plurality of light-receiving elements provided on said light-receiving unit.

20. An equipment according to claim 19, wherein said plurality of light-receiving elements of said light-receiving unit arranged in a scanning direction in which the reflected light travels in said light-receiving unit in response to a scan of the subject by the object light, and said light-receiving unit comprises a charge coupled device having read circuits for outputting the light-receiving signals derived from the light-receiving elements within the light-receiving aperture which are movably set up, said light-receiving aperture comprising at least part of plural light-receiving elements selected from among the plurality of light-receiving elements provided on said light-receiving unit.

21. An equipment according to claim 19, wherein said electronic focusing control unit comprises a plurality of variable gain amplifiers for defining said light-receiving aperture and each of said variable gain amplifiers variably amplifying the light-receiving signal derived from an associated one of the plural light-receiving elements within said light-receiving aperture.

22. An equipment according to claim 1, wherein said electronic focusing control unit comprises:

a plurality of A/D converters, each of said plurality of A/D converters for converting the light-receiving signal in the form of an analog signal derived from an associated one of said plurality of light-receiving elements into a digital light-receiving signal; and delay and addition operation means for relatively delaying and adding the digital light-receiving signals derived from said plurality of A/D converters.

23. An equipment according to claim 22, wherein said electronic focusing control unit comprises an aperture definition means for optionally defining a light-receiving aperture for obtaining the light-receiving signals to be added to each other by said delay and addition operation means on the basis of said digital light-receiving signals, said light-receiving aperture comprising at least part of plural light-receiving elements among the plurality of light-receiving elements provided on said light-receiving unit.

24. An equipment according to claim 23, wherein said delay and addition operation means relatively delays said digital light-receiving signals, which are derived from the plurality of light-receiving elements forming the light-receiving aperture defined by said aperture definition means and are subjected to the digital conversion by said A/D converters, and in addition performs a weighting addition on a variable weighted amount basis.

25. An equipment according to claim 1, wherein said object unit is equipped with a correction plate according to the subject for correcting the light paths of at least one of said object light and said reflected light, said correction plate being one of fixed and interchangeably mounted on said object unit.

26. An equipment according to claim 1, further comprising a display unit to display tomographic images of the subject on the basis of a resultant light-receiving signal involved in emphasis of information of the predetermined point.

* * * * *

Disclaimer 5,579,112—Yuiti Sugiyama; Junji Miyazaki, both of Yamagata, Japan. OPTICAL TOMOGRAPHIC IMAGING EQUIPMENT HAVING A LIGHT SOURCE UNIT FOR GERATING A LIGHT WAVE HAVING A PREDETERMINED COHERENCE LENGTH. Disclaimer filed December 3, 2001, by assignee, Biophotonics Information Laboratories LTD.

Hereby disclaims and dedicates to the Public the term of this patent No. 5,579,112.
(*Official Gazette, March 26, 2002.*)